US 6,627,193 B1

(12) United States Patent
Travis et al.

(10) Patent No.: US 6,627,193 B1
(45) Date of Patent: Sep. 30, 2003

(54) METHODS AND COMPOSITIONS FOR CONTROL OF BLOOD COAGULATION

(75) Inventors: James Travis, Athens, GA (US); Takahisa Imamura, Kumamoto (JP); Jan Potempa, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/482,500

(22) Filed: Jan. 13, 2000

Related U.S. Application Data

(60) Provisional application No. 60/115,869, filed on Jan. 13, 1999.

(51) Int. Cl.[7] .......................... A61K 38/46; C12N 9/50; C12N 9/52

(52) U.S. Cl. .................. 424/94.65; 435/13; 435/23; 435/69.6; 435/219; 435/220; 530/380; 530/829; 514/2

(58) Field of Search .................. 435/220, 13, 69.6, 435/23, 219; 530/380, 829; 514/2; 424/94.65

(56) References Cited

U.S. PATENT DOCUMENTS 5,674,489 A    10/1997   Slungaard ................ 424/94.64
6,017,532 A  *  1/2000   Travis et al. ............ 424/94.65

OTHER PUBLICATIONS

Crawhall et al. Plasma Cystine and Cysteine Concentrations and the Effect of D–Penicillamine and Dietary Treatment. (1968) vol. 44, pp. 330–339.*
Chen et al. Purification and Characterization of a 50–kDa Cysteine Proteinase (Gingipain) from *Porphyromonas gingivalis*. (1992) J. Biol. Chem. 267(26): 18896–18901.*
Alcaraz et al., "Activation of the Protein C pathway in acute sepsis," *Thromb. Res.*, 79(1):83–93 (1995).
Allaart et al., "Increased risk of venous thrombosis in carriers of hereditary protein C deficiency defect," *Lancet*, 341:134–138 (1993).
Ausubel et al., eds., *Current Protocols in Molecular Biology*, John Wiley & Sons, Inc., USA, Title page, 12 pgs. (1994).
Baker, "Clinical Aspects of Disseminated Intravascular Coagulation: A Clinician's Point of View," *Semin. Thromb. Hemostasis*, 15(1):1–57 (1989).
Chase, Jr. et al., "p–Nitrophenyl–p'–guanidinobenzoate HCI: A new active site titrant for trypsin," *Biochem. Biophys. Res. Commun.*, 29(4):508–514 (1967).
Conkling et al., "Tumor Necrosis Factor Induces Tissue Factor–Like Activity in Human Leukemia Cell Line U937 and Peripheral Blood Monocytes," *Blood*, 72(1):128–133 (1988).

Corrigan, Jr., et al., "Changes in the blood coagulation system associated with septicemia," *N. Engl. J. Med.*, 279(16):851–856 (1968).
Cronberg et al., "Disseminated intravascular coagulation in septicemia caused by beta–hemolytic streptococci," *Thromb. Res.*, 3(4):405–411 (1973).
Currie et al., "An unexpected death associated with an acute dentoalveolar abscess—report of a case," *Br. J. Oral Maxillofac. Surg.*, 31(5):296–298 (1993).
Eaton et al., "Proteolytic Processing of Human Factor VIII. Correlation of Specific Cleavages by Thrombin, Factor Xa, and Activated Protein C with Activation and Inactivation of Factor VIII Coagulant Activity," *Biochemistry*, 25(2):505–512 (1986).
Esmon, "The Roles of Protein C and Thrombomodulin in the Regulation of Blood Coagulation," *J. Biol. Chem.*, 264(9):4743–4746 (1989).
Esmon, "Molecular Events that Control the Protein C Anticoagulant Pathway," *Thromb. Haemost.*, 70(1):29–35 (1993).
Esmon, "Inflammation and thrombosis: The impact of inflammation on the protein C anticoagulant pathway," *Haematologica*, 80(Suppl. to No. 2):49–56 (1995).
Foster et al., "The nucleotide sequence of the gene for human protein C," *Proc. Natl. Acad. Sci. USA*, 82:4673–4677 (1985).
Francis, Jr. et al., "Rapid Amidolytic Assay of Protein C in Whole Plasma Using an Activator from the Venom of Agkistrodon Contortrix," *Am. J. Clin. Pathol.*, 87(5):619–625 (1987).
Freyssinet et al., "The effect of phospholipids on the activation of protein C by the human thrombin–thrombomodulin complex," *Biochem. J.*, 238:151–157 (1986).
Fulcher et al., "Proteolytic Inactivation of Human Factor VIII Procoagulant Protein by Activated Human Protein C and its Analogy with Factor V," *Blood*, 63(2):486–489 (1984).
Griffin et al., "Protein C, an Antithrombotic Protein, is Reduced in Hospitalized Patients with Intravascular Coagulation," *Blood*, 60:261–264 (1982).
Harlow et al., *Antibodies, A Laboratory Manual*, Cold Spring Harbor Laboratory Press, Cold Spring Harbor, New York, 9 pgs. (1988).

(List continued on next page.)

*Primary Examiner*—Christopher S. F. Low
*Assistant Examiner*—Holly Schnizer
(74) *Attorney, Agent, or Firm*—Mueting, Raasch & Gebhardt, P.A.

(57) ABSTRACT

Methods for controlling blood coagulation, and suitable pharmaceutical compositions that include a polypeptide that enhances the anticoagulation process (or inhibitors thereof for reversing the anticoagulation process) are provided.

47 Claims, 6 Drawing Sheets-

OTHER PUBLICATIONS

Horie et al., "Enhancement of thrombin–thrombomodulin-catalysed protein C activation by phosphatidylethanolamine containing unsaturated fatty acids: possible physiological significance of phosphatidylethanolamine in anticoagulant activity of thrombomodulin," *Biochem. J., 301*(3):683–691 (1994).

Hosotaki et al., "Activation of Protein C by Arginine–Specific Cysteine Proteinases (Gingipains R) from *Porphyromonas gingivalis*," *Biol. Chem., 380*:75–80 (1999).

Imamura et al., "Pathogenesis of Periodontitis: A Major Arginine–Specific Cysteine Proteinase from *Porphyromonas gingivalis* Induces Vascular Permeability Enhancement through Activation of the Kallikrein/Kinin Pathway," *J. Clin. Invest., 94*:361–367 (1994).

Imamura et al., "Activation of Blood Coagulation Factor X by Arginine–specific Cysteine Proteinases (Gingipain–Rs) from *Porphyromonas gingivalis*," *J. Biol. Chem., 272*(25):16062–16067 (1997).

Kisiel, "Human Plasma Protein C: isolation, characterization and mechanism of activation by α–thrombin," *J. Clin. Invest., 64*:761–769 (1979).

Klein et al., "Purification of a Protein C Activator from the Venom of the Southern Copperhead Snake (*Agkistrodon contortrix contortrix*)," *Biochemistry, 25*(15):4175–4179 (1986).

Kobayashi et al., "Amidolytic Kinetic Assay of Protein C by Selective Spectrophotometry in a Centrifugal Analyzer," *Clin. Chem., 34*(11):2260–2263 (1988).

Levi et al., "Pathogenesis of Disseminated Intravascular Coagulation in Sepsis," *J. Am. Med. Assoc., 270*(8):975–979 (1993).

Maeda et al., "Phathogenic Mechanisms Induced by Microbial Proteases in Microbial Infections," *Biol. Chem., 377*(4):217–226 (1996).

Nakayama, "Domain–Specific Rearrangement between the Two Arg–Gingipain–Encoding Genes in *Porphyromonas gingivalis*: Possible Involvement of Nonreciprocal Recombination," *Microbiol. Immunol., 41*(3):185–186 (1997).

Orthner et al., "Characterization of a Protein C Activator from the Venom of *Agkistrodon contortrix contortrix*," *Biochemistry, 27*(7):2558–2564 (1988).

Pavloff et al., "Molecular Cloning and Structural Characterization of the Arg–gingipain Proteinase of *Porphyromonas gingivalis*: Biosynthesis as a Proteinase–Adhesin Polyprotein," *J. Biol. Chem., 270*(3):1007–1010 (1995).

Pike et al., "Lisine– and Arginine–specific Proteinases from *Porphyromonas gingivalis*: isolation, characterization, and evidence for the existence of complexes with hemagglutinins," *J. Biol. Chem., 269*(1):406–411 (1994).

Pike et al., "Characterization of the Binding Activities of Proteinase–Adhesin Complexes from *Porphyromonas gingivalis*," *J. Bacteriol., 178*(10):2876–2882 (1996).

Potempa et al., "Titration and Mapping of the Active Site of Cysteine Proteinases from *Porphyromonas gingivalis* (Gingipains) using Peptidyl Chloromethanes," *Biol. Chem., 378*(3/4):223–230 (1997).

Potempa et al., "Comparative Properties of Two Cysteine Proteinases (Gingipains R), the Products of Two Related but Individual Genes of *Porphyromonas gingivalis*," *J. Biol. Chem., 273*(34):21648–21657 (1998).

Sakoda et al., "Determination of the Best–Fit Values of Kinetic Parameters of the Michaelis–Menten Equation by the Method of Least Squares with the Taylor Expansion," *J. Biochem., 80*(3):547–555 (1976).

Salem et al., "Isolation and Characterization of Thrombomodulin from Human Placenta," *J. Biol. Chem., 259*(19):12246–12251 (1984).

Stearns et al., "The Interaction of a $Ca^{2+}$–dependent Monoclonal Antibody with the Protein C Activation Peptide Region," *J. Biol. Chem., 263*(2):826–832 (1988).

Suzuki et al., "Inactivation of Human Coagulation Factor V by Activated Protein C," *J. Biol. Chem., 258*(3):1914–1920 (1983).

Taylor, Jr. et al., "Protein C Prevents the Coagulopathic and Lethal Effects of *Escherichia coli* Infusion in the Baboon," *J. Clin. Invest., 79*:918–925 (1987).

Tracy et al., "Proteolytic Alterations of Factor Va Bound to Platelets," *J. Biol. Chem., 258*(1):662–669 (1983).

Travis et al., "Are bacterial proteinases pathogenic factors?," *Trends Microbiol., 3*(10):405–407 (1995).

Walker et al., "The inhibition of blood coagulation by activated protein C through the selective inactivation of activated factor V," *Biochim. Biophys. Acta., 571*(2):333–342 (1979).

Warr et al., "Disseminated Intravascular Coagulation in Rabbits Induced by Administration of Endotoxin or Tissue Factor: Effect of Anti–Tissue Factor Antibodies and Measurement of Plasma Extrinsic Pathway Inhibitor Activity," *Blood, 75*(7):1481–1489 (1990).

Wegrzynowicz et al., "Prothrombin Activation by a Metalloprotease from *Staphylococcus aureus*," *J. Clin. Microbiol., 12*(2):138–139 (1980).

Yoshikawa et al., "Bacteriodaceae Bacteremia with Disseminated Intravascular Coagulation," *Am. J. Med., 56*:725–728 (1974).

Imamura, "Dependence of Vascular Permeability Enhancement on Cysteine Proteinases in Vesicles of *Porphyromonas gingivalis*," *Infection and Immunity, vol. 63, No. 5*, pp. 1999–2003 (May 1995).

Imamura, "Effect of Free and Vesicle–Bound Cysteine Proteinases of *Porphyromonas gingivalis* on Plasma Clot Formation: Implications for Bleeding Tendency at Periodontitis Sites," *Infection and Immunity, vol. 63, No. 12*, pp. 4877–4882 (Dec. 1995).

Imamura, "Comparison of Pathogenic Properties Between Two Types of Arginine–Specific Cysteine Proteinases (gingipains–R) from *Porphyromonas gingivalis*," *Microbial Pathogenesis, vol. 29*, pp. 155–163 (2000).

Imamura, "Activation of Human Prothombin by Arginine–specific Cysteine Proteinases (Gingipains R) from *Prophyromonas gingivalis*," *Journal of Biological Chemistry, vol. 276, No. 22*, pp. 18984–18991 (Jun. 2001).

Imamura, "Activation of Blood Coagulation Factor IX by Gingipains R, Arginine–Specific Cysteine Proteinases from *Porphyromonas gingivalis*," *Biochemical Journal, vol. 353*, pp. 325–331 (2001).

Law et al., "The Internal Thioester and the Covalent Binding Properties of the Complement Proteins C3 and C4," *Protein Science, vol. 6, No. 2*, pp. 263–274 (1997) [retrieved on Oct. 1, 2001]. Retrieved from the Internet: <URL: http.//www-.prosci.uci.edu/Articles/Vol6/issue2/6335/6335.html>, pp. 1–17.

National Center for Biotechnology Information, National Library of Medicine, National Institutes of Health, GenBank Locus No. PGU85038, Accession No. U85038, "*Porphyromonas gingivalis* arginine–specific cysteine proteinase RGP–2 (rgp2) gene, complete cds," [online], Bethesda, MD [retrieved on Dec. 14, 2001]. Retrieved from the Internet:<URL: http://www.ncbi.nlm.nih.gov/entrez/query.fcgi?cmd=Retrieve&db=nucleotide&list_uids=1814393&dopt=GenBank>, 2 pgs.

National Center for Biotechnology Information, National Library of Medicine, National Institutes of Health, GenBank Locus #PGU15282, Accession # U15282, "*Porphyromonas gingivalis* Arg–gingipain–1 proteinase gene, complete cds," [online], Bethesda, MD [retrieved on Dec. 14, 2001]. Retrieved from the Internet:<URL: http://www.ncbi.nlm.nih.gov/entrez/query.fcgi?cmd=Retrieve&db=nucleotide&list_uids=557067&dopt=GenBank>, 4 pgs.

\* cited by examiner

```
     Seq ID NO:1
                                                              YTP VEEKQNGRMI
  14 VIVAKKYEGD IKDFVDWKNQ RGLRTEVKVA EDIASPVTAN AIQQFVKQEY EKEGNDLTYV
  74 LLVGDHKDIP AKITPGIKSD QVYGQIVGND HYNEVFIGRF SCESKEDLKT QIDRTIHYER
 134 NITTEDKWLG QALCIASAEG GPSADNGESD IQHENVIANL LTQYGYTKII KCYDPGVTPK
 194 NIIDAFNGGI SLVNYTGHGS ETAWGTSHFG TTHVKQLTNS NQLPFIFDVA CVNGDFLFSM
 254 PCFAEALMRA QKDGKPTGTV AIIASTINQS WASPMRGQDE MNEILCEKHP NNIKRTFGGV
 314 TMNGMFAMVE KYKKDGEKML DTWTVFGDPS LLVRTLVPTK MQVTAPAQIN LTDASVNVSC
 374 DYNGAIATIS ANGKMFGSAV VENGTATINL TGLTNESTLT LTVVGYNKET VIKTINTNGE
 434 PNPYQPVSNL TATTQGQKVT LKWDAPSTKT NATTNTARSV DGIRELVLLS VSDAPELLRS
 494 GQAEIVLEAH DVWNDGSGYQ ILLDADHDQY GQVIPSDTHT LWPNCSVPAN LFAPFEYTVP
 554 ENADPSCSPT NMIMDGTASV NIPAGTYDFA IAAPQANAKI WIAGQGPTKE DDYVFEAGKK
 614 YHFLMKKMGS GDGTELTISE GGGSDYTYTV YRDGTKIKEG LTATTFEEDG VATGNHEYCV
 674 EVKYTAGVSP KVCKDVTVEG SNEFAPVQNL TGSAVGQKVT LKWDAPNGTP NPNPNPNPNP
 734 GTTTLSESFE NGIPASWKTI DADGDGHGWK PGNAPGIAGY NSNGCVYSES FGLGGIGVLT
 794 PDNYLITPAL DLPNGGKLTF WVCAQDANYA SEHYAVYASS TGNDASNFTN ALLEETITAK
 854 GVRSPEAIRG RIQGTWRQKT VDLPAGTKYV AFRHFQSTDM FYIDLDEVEI KANGKRADFT
 914 ETFESSTHGE APAEWTTIDA DGDGQGWLCL SSGQLDWLTA HGGTNVVASF SWNGMALNPD
 974 NYLISKDVTG ATKVKYYYAV NDGFPGDHYA VMISKTGTNA GDFTVVFEET PNGINKGGAR
1034 FGLSTEANGA KPOSVWIERT VDLPAGTKYV AFRHYNCSDL NYILLDDIQF TMGGSPTPTD
1094 YTYTVYRDGT KIKEGLTETT FEEDGVATGN HEYCVEVKYT AGVSPKECVN VTINPTQFNP
1154 VKNLKAQPDG GDVVLKWEAP SAKKTEGSRE VKRIGDGLFV TIEPANDVRA NEAKVVLAAD
1214 NVWGDNTGYO FLLDADHNTF GSVIPATGPL FTGTASSNLY SANFEYLIPA NADPVVTTQN
1274 IIVTGQGEVV IPGGVYDYCI TNPEPASGKM WIAGDGGNQP ARYDDFTFEA GKKYTFTMRR
1334 AGMGDGTDME VEDDSPASYT YTVYRDGTKI KEGLTETTYR DAGMSAQSHE YCVEVKYAAG
1394 VSPKVCVDYI PDGVADVTAQ KPYTLTVVGK TITVTCQGEA MIYDMNGRRL AAGRNTVVYT
1454 AQGGYYAVMV VVDGKSYVEK LAVK
```

*Fig. 6*

```
Seq ID NO:3 ──▶ YTPVEEKENGRMIVIVAKKYEGDIKDFVDWKNQRG    35
Seq ID NO:2 ──▶ .....Q............................    35

LRTEVKVAEDIASPVTANAIQQFVKQEYEKEGNDL    70
                ..................................    70

TYVLLVGDHKDIPAKITPGIKSDQVYGQIVGNDHY   105
                ..................................   105

NEVFIGRFSCESKEDLKTQIDRTIHYERNITTEDK   140
                ..................................   140

WLGQALCIASAEGGPSADNGESDIQHENVIANLLT   175
                ..................................   175

QYGYTKIIKCYDPGVTPKNIIDAFNGGISLVNYTG   210
                ..................................   210

HGSETAWGTSHFGTTHVKQLTNSNQLPFIFDVACV   245
                ..................................   245

NGDFLFSMPCFAEALMRAQKDGKPTGTVAIIASTI   280
                ..................................   280

DQYWAPPMRGQDEMNEILCEKHPNNIKRTFGGVTM   315
                N·S··S····························   315

NGMFAMVEKYKKDGENMLDTWTVFGDPSLLVRTLV   350
                ····K·····························   350

PTEMQVTAPANISASAQTFEVACDYNGAIATLSDD   285
                ··K······Q·NLTDASVN·S······I·AN       285

GDMVGTAIVKDGKAIIKLNESIADETNLTLTVVGY   420
                ·K·F·S·V·EN·T·T·N·T-GLTN·ST·······   419

NKvtvikdvkveg···avriategktytekvivk   507
                ··E····TINTN····GIRELVLLSVSDAPELLR   492
```

METHODS AND COMPOSITIONS FOR CONTROL OF BLOOD COAGULATION

CROSS-REFERENCE TO RELATED APPLICATIONS

The present application claims the benefit of U.S. Provisional Patent Application Serial No. 60/115,869, filed on Jan. 13, 1999, which is incorporated herein by reference.

STATEMENT OF GOVERNMENT SUPPORT

This work was supported by National Institute of Health grant DE 09761. The government may have certain rights in the invention.

BACKGROUND

The control of bleeding and clotting are extremely important in medical and surgical procedures. Protein C (PC), a vitamin-K-dependent plasma glycoprotein, is of major physiological importance in the control of bleeding. Protein C exists in two forms, an inactive or nascent form and an active form. Inactive protein C is composed of two polypeptide chains with a molecular weight of 62 kDa. It is present as a serine proteinase zymogen whose limited proteolysis results in the release of a dodecapeptide from the N-terminus of the heavy chain and the conversion of the zymogen form to activated PC (APC). PC activation is normally catalyzed by its interaction with a 1:1 stoichiometric complex of thrombin with thrombomodulin, a protein expressed on endothelial cells under physiological conditions.

APC is a natural anticoagulant that degrades the activated forms of the clotting cofactors V and VIII (i.e., Va and VIIIa), thereby terminating the procoagulant activity of Factors Va and VIIa, in the presence of phospholipids and a cofactor, protein S. Thus, APC negatively regulates the blood coagulation system. The thrombotic tendency of patients, as represented by a tendency for blood clot formation, with either a PC-deficiency or genetic abnormality clearly demonstrates the importance of the PC pathway in the control of coagulation.

Decreased plasma levels of PC have been reported in patients with disseminated intravascular coagulation (DIC) or in sepsis (i.e., the presence in the blood or other tissues of pathogenic microorganisms or their toxins, also referred to as septicemia), which precludes DIC. In parallel with this effect, increased levels of APC complexed with 1-proteinase inhibitor or APC inhibitor have been observed in septic patients, indicating consumption of the active enzyme. Recent studies have shown that monocyte derived tissue factor initiates the extrinsic coagulation pathway in sepsis or DIC. Accordingly, any thrombin generated would form a complex with thrombomodulin and activate PC, resulting in a significant decrease in concentration of this anticoagulant factor. Since endotoxin and/or endotoxin-induced tumor necrosis factor can stimulate monocytes to express tissue factor, the tendency has been to recognize lipopolysaccharide as the primary bacterial agent responsible for decreased PC levels in sepsis. Besides endotoxin, however, bacteria release a variety of proteinases, some of which are known to activate coagulation factors, including prothrombin, factor XII and prekallikrein.

SUMMARY OF THE INVENTION

The present invention provides methods for controlling blood coagulation, and suitable pharmaceutical compositions.

In one embodiment is a method for producing activated protein C in a medium by contacting the medium with an effective amount of an arginine-specific cysteine proteinase of bacterial origin.

In a second embodiment is a method for producing activated protein C in blood by contacting the blood with an effective amount of a polypeptide represented by SEQ ID NO:1, SEQ ID NO:2, or SEQ ID NO:3, active fragments or active modifications thereof.

In a third embodiment is a method for producing activated protein C in blood by contacting the blood with an effective amount of a polypeptide encoded by a polynucleotide, the complement of which hybridizes to nucleotides encoding the polypeptide of SEQ ID NO:1, SEQ ID NO:2, or SEQ ID NO:3 under standard hybridization conditions.

In a fourth embodiment is a method of inhibiting blood coagulation in a patient by administering an effective anticoagulant amount of an argimne-specific cysteine proteinase of bacterial origin.

In a fifth embodiment is a method of inhibiting blood coagulation in a patient by administering an effective anticoagulant amount of a polypeptide represented by SEQ ID NO:1, SEQ ID NO:2, or SEQ ID NO:3, active fragments or active modifications thereof.

In a sixth embodiment is a method of inhibiting blood coagulation in a patient by administering an effective anticoagulant amount of a polypeptide encoded by a polynucleotide, the complement of which hybridizes to nucleotides encoding the polypeptide of SEQ ID NO:1, SEQ ID NO:2, or SEQ ID NO:3 under standard hybridization conditions.

In a seventh embodiment is an anticoagulant composition that includes an effective amount of an arginine-specific cysteine proteinase of bacterial origin, or salt thereof, and a pharmaceutically acceptable carrier.

In an eighth embodiment is an anticoagulant composition that includes an effective amount of a polypeptide represented by SEQ ID NO:1, SEQ ID NO:2, or SEQ ID NO:3, active fragments or active modifications thereof.

In a ninth embodiment is an anticoagulant composition that includes an effective amount of a polypeptide encoded by a polynucleotide, the complement of which hybridizes to nucleotides encoding the polypeptide of SEQ ID NO:1, SEQ ID NO:2, or SEQ ID NO:3 under standard hybridization conditions.

In a tenth embodiment is a method for reversing anticoagulation in a medium by contacting the medium with an inhibitor of an arginine-specific cysteine proteinase of bacterial origin.

In an eleventh embodiment is an anticoagulant reversing composition that includes an effective amount of an inhibitor of an arginine-specific cysteine proteinase of bacterial origin, or salt thereof, and a pharmaceutically acceptable carrier.

In a twelfth embodiment is a method for treating septicemia in a patient by administering an effective amount of an inhibitor of an arginine-specific cysteine proteinase of bacterial origin, or salt thereof. Preferably, the septicemia is induced by pathogenic bacteria.

In yet another embodiment is a method for treating disseminated intravascular coagulation in a patient by administering an effective amount of an inhibitor of an arginine-specific cysteine proteinase of bacterial origin, or salt thereof. Preferably, the disseminated intravascular coagulation is induced by pathogenic bacteria.

Definitions

"Polypeptide" as used herein refers to a polymer of amino acids and does not refer to a specific length of a polymer of amino acids. Thus, for example, the terms peptide, oligopeptide, protein, and enzyme are included within the definition of polypeptide. This term also includes post-expression modifications of the polypeptide, for example, glycosylations, acetylations, phosphorylations, and the like. "Peptidase," "proteinase," and "protease" are used interchangeably to refer to enzymes and are encompassed within the definition of polypeptide.

The term "isolated" means that a polypeptide is either removed from its natural environment or synthetically derived. Preferably, the polypeptide is purified, i.e., essentially free from any other polypeptides and associated cellular products or other impurities.

The terms "hybridizes," "hybridizing," and "hybridization" mean that a single stranded polynucleotide forms a noncovalent interaction with a complementary polynucleotide under certain conditions, as described herein.

BRIEF DESCRIPTION OF THE DRAWINGS

FIGS. 2A and 2B. Kinetic study of PC activation by gingipains R. The initial velocities of PC activation by RgpA (A) or RgpB (B) were determined under the conditions described in "Experimental Procedures." The concentrations of a proteinase were 0.5 nM respectively. $[S]_o/v$ vs. $[S]_o$ plots of the data were shown in each "inset."

FIG. 6. Amino acid sequence of the 95 kDa RgpA (also referred to as HRGP) (SEQ ID NO:1).

FIG. 7. Amino acid sequence of the 50 kDa catalytic domain of the 95 kDa RgpA (SEQ ID NO:2) and amino acid sequence of the 50 kDa RgpB (SEQ ID NO:3). Amino acids in SEQ ID NO:2 that are identical to the corresponding amino acids in SEQ ID NO:3 are marked by bullets. A single gap (–) in (SEQ ID NO:2) was introduced to improve alignment. An underlined fragment of RgpB (SEQ ID NO:3) has not been sequenced, and it is assumed that it is covalently modified either on a Lys or Asp residue. The fragment of residues (434–489) in the C-terminal region of the initial polypeptide chain of RgpB (SEQ ID NO:3) and the fragment of residues (433–474) of SEQ ID NO:2 share no similarity, were excluded from alignment, and are marked with dots.

DETAILED DESCRIPTION OF PREFERRED EMBODIMENTS

Figure 1A:
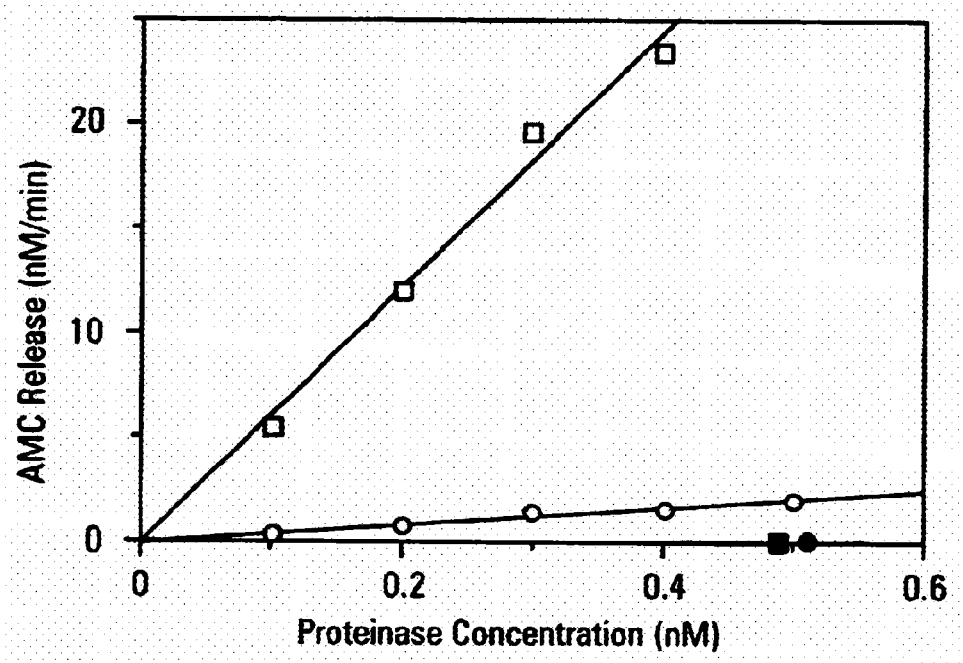

The present invention provides methods for controlling blood coagulation, and suitable pharmaceutical compositions. The present invention is based on the discovery that a polypeptide, preferably, an arginine-specific cysteine proteinase of bacterial origin, promotes the activation of protein C, and hence, the inhibition of blood coagulation. Antibodies and other inhibitors of the activity of such polypeptides can be used to reverse the anticoagulation process. Cornpositions containing such polypeptides or inhibitors find utility in a variety of clinical settings that require the control of blood coagulation, i.e., either to promote anticoagulation or to reverse the anticoagulation process. This includes, for example, the treatment of myocardial infarction, pulmonary embolism, cerebrovascular disease, and the like.

Thus, the present invention provides a method of inhibiting blood coagulation (i.e., promoting anticoagulation) in a patient through the administration of a polypeptide, as well as a method of reversing the anticoagulation process (i.e., promoting blood coagulation or reversing the inhibition of blood coagulation) in a patient through the administration of an antibody or other inhibitor to such polypeptide. Compositions containing such polypeptides and inhibitors are also provided. As used herein, "patient" refers to mammals such as primates, including humans, sheep, horses, cattle, pigs, dogs, cats, rats, and mice.

One embodiment of a method of the present invention involves inhibiting blood coagulation by administering to a patient an effective amount of an arginine-specific cysteine proteinase of bacterial origin, preferably one that includes a catalytic domain and a hemagglutinin/adhesion domain. Another embodiment of a method of the present invention involves producing activated protein C in blood by contacting the blood with an effective amount of an arginine-specific cysteine proteinase of bacterial origin, preferably one that includes a-catalytic-domain and a hemagglutimin/adhesion domain. A particularly preferred arginine-specific cystein& proteinase has the sequence represented by SEQ ID NO: 1, whether naturally occurring or recombinant. As used in this context, an "effective amount" is an amount effective to inhibit coagulation of blood and/or increase the concentration of activated protein C in blood. These amounts can be determined by one of skill in the art.

The present invention also provides a method of inhibiting blood coagulation in vitro in a medium, e.g., a sample of whole blood, as well as a method of producing activated protein C (APC) in vitro in a medium, e.g., a sample of whole blood. These methods preferably involve contacting the blood with an effective amount of a polypeptide, preferably, an arginine-specific cysteine proteinase of bacterial origin, and more preferably an arginine-specific cysteine proteinase that includes a catalytic domain and a hemagglutinin/adhesion domain. As used in this context, an "effective amount" is an amount effective to inhibit coagulation, or generate large amounts of APC that can be used for the treatment of various disorders, such as septic shock, for example. These amounts can be determined by one of skill in the art.

For these in vitro methods, the medium can be whole blood, blood plasma, and other biological samples in which blood coagulation is undesirable. In this way, whole blood, plasma samples, and other biological samples can be stored for longer periods of time with a reduced incidence of blood clotting. Also, large amounts of APC can be generated in vitro and harvested for use in the treatment of disorders requiring infusion of large amounts of APC, such as septic shock (see, Taylor et al., *J. Clin. Invest.*, 79, 918–925 (1987)).

In one embodiment of a method of reversing the inhibition of coagulation (i.e., reversing anticoagulation or promoting blood coagulation) involves administering to a patient an effective amount of an inhibitor of an arginine-specific cysteine proteinase of bacterial origin, preferably one that includes a catalytic domain and a hemagglutinin/adhesion domain. A particularly preferred arginine-specific cysteine proteinase has the sequence represented by SEQ ID NO: 1, whether naturally occurring or recombinant. As used in this context, an "effective amount" is an amount effective to reverse the anticoagulation process. These amounts can be determined by one of skill in the art.

The present invention also provides a method of reversing the inhibition of blood coagulation in vitro in a medium, e.g., a sample of whole blood. This method preferably involves contacting the blood with an effective amount of a polypeptide, preferably, an arginine-specific cysteine proteinase of bacterial origin, and more preferably an arginine-specific cysteine proteinase that includes a catalytic domain and a hemagglutinin/adhesion domain. As used in this context, an "effective amount" is an amount effective to reverse the anticoagulation process. These amounts can be determined by one of skill in the art. For these in vitro methods, the medium can be whole blood, blood plasma, and other biological samples in which blood anticoagulation is undesirable.

The polypeptide is typically provided in its isolated form and preferably in a purified form, i.e., a form that is substantially free of other proteins, lipids, and carbohydrates with which they are typically associated. Preferably, a purified polypeptide preparation will generally yield a single major band on a polyacrylamide gel for each subunit of desired protein. The polypeptide can be naturally occurring, synthetic, i.e., chemically produced, or recombinant, i.e., biologically cloned. It can be a full length, i.e., whole protein, or a peptide fragment thereof. As used herein, a "fragment" refers to a portion of a longer amino acid sequence. The purified polypeptide can be an analog or modification of the naturally occurring protein. As used herein, an "analog" or "modification" refers to a polypeptide that is substantially the same as another but which has different amino acids at certain locations in the amino acid sequence. A protein, fragment, or modification thereof can also be chemically modified to produce an adduct that can be used in the methods and compositions of the present invention. Additionally, mutants and adducts (referred to herein as "modifications") of peptide fragments, whether produced by isolation, synthetic, or recombinant techniques, can be used in the methods and compositions of the present invention. The modifications and fragments are useful as long as they retain anticoagulant activity (i.e., are "active"), preferably substantially the same anticoagulant activity as the original proteinase. That is, the active fragments and active modifications of the proteinases described herein, are useful in the methods and compositions of the present invention as long as they enhance the activation of protein C to form APC.

Suitable polypeptides used herein for the anticoagulant compositions and for developing inhibitors, such as antibodies, are preferably arginine-specific cysteine proteinases of bacterial origin. From *Porphyromonas gingivalis* HG66 two arginine-specific cysteine proteinases have been isolated. They are referred to herein as RgpA and RgpB, also referred to in the literature as the 95-kDa gingipain R (HRGP) and the 50 kDa-gingipain R (RGP-2), respectively (J. Potempa et al., *J. Biol. Chem.*, 273, 21648–21657 (1998) and N. Pavloffet al., *J. Biol. Chem.*, 270 1007–1010 (1995)), which are products of two related but distinct genes. While RgpA (i.e., the 95 kDa proteinase or HRGP, SEQ ID NO:1) is a non-covalent complex of the catalytic and hemagglutinin/adhesion domains, RgpB (SEQ ID NO:3) has only been found to occur as a truncated protein with an amino acid sequence essentially identical to the catalytic domain of RgpA (SEQ ID NO:2). Both enzymes have activity restricted to Arg-Xaa peptide bonds and can activate plasma prekallikrein and blood coagulation factor X.

As shown in the Examples below, each enzyme (the 95 kDa RgpA and the 50 kDa RgpB) activates human protein C in a dose- and incubation time-dependent manner. Interestingly, the form of enzyme being composed of a non-covalent complex containing both catalytic and adhesion domains (RgpA) produces activated protein C 14-fold more efficiently than RgpB, which containes the catalytic domain alone. The kcat/Km value of RgpA is 18-fold higher than that of RgpB and comparable to that of the thrombin-thrombomodulin complex, the physiological activator of protein C. RgpA catalyzed protein C activation is augmented 1.4-fold by phospholipids, ubiquitous cell membrane components. Furthermore, RgpA activates protein C in plasma and this results in a decrease of the protein C concentration in plasma, which is often observed in patients with sepsis during the development of disseminated intravascular coagulation (DIC).

Until now no bacterial proteinase has been shown to activate PC and, with the exception of factors involved in the coagulation cascade, the activation of this anticoagulant factor has been shown to be catalyzed only by snake venom proteinases. See, for example, C. L. Orthner et al., *Biochemistry*, 27, 2558–2564 (1988).

Thus, for certain embodiments of the present invention, the polypeptide is an arginine-specific cysteine proteinase of bacterial origin. Preferably, this proteinase includes a catalytic domain and a hemagglutinin/adhesion domain. More preferably, the polypeptide has a molecular weight of about 90–100 KDa. For certain embodiments, the polypeptide is represented by SEQ ID NO:1, SEQ ID NO:2, or SEQ ID NO:3, active fragments or active modifications thereof.

Alternatively, a polypeptide useful in some aspects of the invention is encoded by a polynucleotide, the complement of which hybridizes to nucleotides encoding RgpA (HRGP) or RgpB. An example of a nucleotide sequence that encodes the catalytic and the hemagglutination/adhesion domains of RgpA (HRGP) is nucleotides 1630 to 6063 of Genbank accession number U15282. An example of a nucleotide sequence that encodes the catalytic domain of RgpA (HRGP) is nucleotides 1630 to 3105 of Genbank accession number U15282. An example of a nucleotide sequence that encodes RgpB is nucleotides 923 to 3133 of Genbank accession number U85038.

Individual wild-type microorganisms can be screened for the presence of the nucleotide sequences. Screening methods include, for instance, hybridization of polynucleotides immobilized on a membrane with a detectably labeled probe. Standard hybridizing conditions use hybridization buffer (2×Denhardt's solution, 6×SSC, 0.4% SDS (w/v), 500 mg/ml salmon sperm DNA) containing labeled probe. Hybridization is allowed to occur at 42° C. for at least 4 hours. The membrane is washed at 48° C. in a solution containing 2×SSC and 0.05% SDS. SSC at a dilution of 1× is 150 mM NaCl, 15 mM sodium citrate, pH 7.0. Preferably, a probe will hybridize to the nucleotide sequence set forth at nucleotides 1630 to 3105 of Genbank accession number U15282, or nucleotides 923 to 3133 of Genbank accession number U85038.

Preferred probes for identifying polynucleotides encoding an arginine-specific cysteine protease that can be used in the present invention are polynucleotides complementary to the nucleotide sequence set forth at nucleotides 1630 to 3105 of Genbank accession number U15282, or nucleotides 923 to 3133 of Genbank accession number U85038. A probe is typically no less than about 20 bases. Methods of detectably labeling a probe are known to the art. The polynucleotide that is identified by the probe is further analyzed using methods known to one of skill in the art to determine if it encodes an arginine-specific cysteine protease.

The inhibitor of the activity of the polypeptides described herein can be any of a variety of synthetic or naturally occurring inhibitors, including antibodies, which can be polyclonal or monoclonal. Laboratory methods for producing polyclonal and monoclonal antibodies are known in the art (see, for instance, E. Harlow et al., *Antibodies: A laboratory manual*, Cold Spring Harbor Laboratory Press, Cold Spring Harbor (1988) and R. M. Ausubel, ed., *Current Protocols in Molecular Biology* (1994).

A polypeptide of the invention, including structurally similar polypeptides and analogs (i.e., modifications) and fragments of either of them, can be used to produce monoclonal and polyclonal antibodies using methods well known in the art. Fragments that are not themselves antigenic can be coupled to an immunogenic carrier polypeptide to initiate an immune response in the host animal or cell. Such non-antigenic fragments, known as haptens, react specifically with an antibody but do not stimulate antibody production unless complexed with a carrier polypeptide. Linking the hapten to a carrier polypeptide produces an immunogen that stimulates antibody production against the hapten. The hapten can be chemically coupled to the carrier polypeptide or fusion polypeptide can be produced using recombinant genetic methods.

The anticoagulant compositions (i.e., compositions containing a polypeptide) described herein are useful in in vivo and in vitro applications. The anticoagulant compositions of the present invention are useful not only in the anticoagulant therapy of individuals having thrombotic conditions or in prophylactic applications, i.e., in in vivo applications, but are useful whenever inhibition of blood coagulation is required such as to prevent coagulation of stored whole blood and to prevent coagulation in other biological samples for testing or storage, i.e., in vitro applications. Thus, the polypeptide composition of this invention can be added to, or contacted with, any medium in which it is desired that blood coagulation be inhibited. Furthermore, the compositions of the present invention can be used to generate large amounts of APC either in vivo or in vitro (and harvested) for use in the treatment of disorders requiring infusion of APC.

Anticoagulant therapy is indicated for the treatment and prevention of a variety of thrombotic conditions, particularly coronary artery and cerebrovascular disease. Specific examples of clinical settings in which the compositions of the present invention can be used include treatment of myocardial infarction, pulmonary embolism, cerebrovascular disease, and the like. For example, they can be used in the treatment of venous thrombosis and thromboembolic disease, arterial thrombosis and thromboembolic disease, myocardial infarctions, pulmonary embolism, cerebrovascular disease, thrombotic occlusions during and subsequent to thrombolytic therapy or angioplastic therapy and, in general, any other such conditions for which anticoagulant therapy is indicated. Such conditions include, but are not limited to, thrombotic complications of other diseases, for example, cancer, tumor metastasis, diabetes, chronic inflanmmation, sepsis, shock, stroke, and other conditions where preventative or prophylactic anticoagulant effects are desired.

In one particular application, the anticoagulant compositions (i.e., containing a polypeptide) of the present invention can be administered along with conventional compositions used in thrombolytic therapy. For example, they can be administered along with urokinase, streptokinase, or tissue plasminogen activator. In this way blood clots can be dissolved by the thrombolytic compositions and further clotting can be avoided by the anticoagulant compositions of the present invention.

For these purposes, an effective amount of the anticoagulant polypeptide described above or a pharmaceutically acceptable salt thereof is administered to a patient in need thereof. By "effective amount" is meant that a quantity of the polypeptide described herein (or a pharmaceutically acceptable salt or salts thereof) sufficient to alleviate the condition for which it is being administered is used.

Similarly, the anticoagulant reversing compositions described herein (i.e., containing an antibody or other inhibitor of the activity of the polypeptides described herein) are useful in in vivo and in vitro applications. The antibodies or other inhibitors would block the activation or Protein C and allow the regulation of coagulation events. That is, while activated protein C will destroy coagulation factors and reduce clotting, an antibody or other inhibitor to the polypeptides described herein (e.g., RgpA) would keep this protein intact and allow the maintenance of clotting. This would be important in both sepsis and disseminated intravascular coagulation (multiple small clots).

For these purposes, an effective amount of the antibody or other inhibitor (or a pharmaceutically acceptable salt thereof) is administered to a patient in need thereof. By "effective amount" is meant that a quantity of the inhibitor described herein (or a pharmaceutically acceptable salt thereof) sufficient to alleviate the condition for which it is being administered is used.

Although the compositions of this invention (whether they are anticoagulant or anticoagulant reversing compositions) may be administered orally, parenteral administration is preferred. These modes of administration include, for example, subcutaneous, intravenous, intramuscular, and intraperitoneal. They also include administration by depot injection or by implant preparation formulated using polymers or synthetic silicones, for example, in such a manner as to permit a sustained release of the active ingredient. Preferably, the compositions of the present invention are administered intravenously.

The choice of pharmaceutically acceptable carrier for administration of the compositions is determined by the route of administration selected. For example, if the compositions are administered orally as by means of tablets, capsules, powders, suspensions, solutions, syrups and the like, such compositions utilize pharmaceutically acceptable carriers containing materials such as diluents, binders, lubricants, disintegrators, buffering agents, surfactants, emulsifing agents, dispersants, flavoring agents, and the like. For parenteral administration acceptable carriers include water, sesame oil, groundnut oil, aqueous propylene glycol, N,N'-dimethylformamide, and the like. Other oils that can be employed in these preparations are those of petroleum, animal, vegetable, or synthetic origin, for example, peanut oil, soybean oil, and mineral oil. For injectable compositions, water, saline, aqueous dextrose and related sugar solutions, ethanol, and glycols such as propylene glycol or polyethylene glycol are prefefred carriers.

The polypeptide can be administered in the form of a pharmaceutically acceptable salt. These include, for example, acid addition salts derived from inorganic acids such as hydrochloric, phosphoric, phosphorous, nitric, sulfuiric, hydrobromic, hydriodic acid and the like. Additionally, such salts can be derived from organic acids such as aliphatic mono and dicarboxylic acids, phenyl-substituted alkanoic acids, hydroxyalkanoic and alkandioic acids, for example. Therefore, such pharmaceutically acceptable salts include sulfate, bisulfate, chloride, bromide, iodide, fluoride, nitrate, phosphate, acetate, formate, propionate, caprate, fumarate, maleate, benzoate, chlorobenzoate, methylbenzoate, dinitrobenzoate, hydroxybenzoate, phthalate, benzenesulfonate, phenylacetate, phenylpropionate, citrate, malate, tanrate, and the like.

EXAMPLES

The present invention is illustrated by the following examples. It is to be understood that the particular examples, materials, amounts, and procedures are to be interpreted broadly in accordance with the scope and spirit of the invention as set forth herein.

Experimental Procedures

Materials. Soybean trypsin inhibitor (SBTI), antipain, benzoyl-L-arginine-p-nitroanilide (BApNA) and tosyl-L-lysine chloromethylketone (TLCK) were purchased from Sigma Chemical Co. (St. Louis, Mo.). Platelin$^{AE}$ (rabbit brain phospholipids) were obtained from Organon Teknika, Co. (Durham, N.C.). D-Phe-L-Pro-L-Arg-chloromethylketone (FPR-ck) was acquired from Bachem Biosci. Inc. (King of Prussia, Pa.), while purified human PC and purified human APC were from The Institute for Chemo-Sero Therapy (Kumamoto, Japan). PC activator from the venom of Southern copperhead snake, Agkistrodon conitortrix contortrix (ACC-PCA) was bought from Calbiochem (La Jolla, Calif.) and anti-human PC sheep IgG was from Cedarlane, (Ontario, Canada). t-Butyloxycarbonyl-L-Leu-L-Ser-L-Thr-L-Arg-4-Methyl-Coumaryl-7-Amide (Boc-Leu-Ser-Thr-Arg-MCA) (SEQ ID NO:4) was obtained from the Peptide Institute (Osaka, Japan). p-Nitrophenyl-p'-guanidinobenzoate was from Nacalai tesque (Kyoto, Japan), while all other chemicals were ordered from Wako Pure Chemicals (Osaka, Japan). Normal human platelet poor-plasma from healthy volunteers was prepared by centrifugation of a mixture of 9 volumes (vol) of freshly drawn blood and 1 vol of 3.8% (wt/vol) sodium citrate.

Proteinase purifcation. RgpA and RgpB were isolated according to the method described by Pike et al., *J. Biol. Chem.*, 269, 406–411 (1994). The amount of active enzyme in each purified rproteinase was determined by active site titration using FPR-ck (J. Potempa et al., *Biol. Chem.*, 378, 223–230 (1997)).

Activation of proteinases. Each gingipain R was activated with 10 mM cysteine in 0.2 M Hepes buffer, pH 8.0, containing 5 mM $CaCl_2$ at 37° C. for 10 minutes (min). The activated proteinase (0.1 $\mu$M) was then diluted with 50 mM Tris-HCl, pH 7.6 containing 100 mM NaCl and 2 mM $CaCl_2$ prior to use.

Kinetic Analysis of PC Activation. PC, dissolved in 90 $\mu$l of 50 mM Tris-HCl, pH 7.6, containing 100 mM NaCl and 2 mM $CaCl_2$, was incubated with 10 $\mu$l of either of the activated gingipains R (final enzyme and cysteine concentration 0.1 nM and 1 mM, respectively) at 37° C. for 30, 60, 90, 120 or 150 seconds. Then, 500 $\mu$l of 50 mM Tris-HCl, pH 7.6, containing 100 mM NaCl and 2 mM $CaCl_2$, supplemented with 2 FM antipain, was added to the reaction mixture. At this concentration anipain inhibits the cysteine prbteinase activity completely, without affecting the amidolytic activity of APC. After addition of 10 $\mu$l of an APC-specific substrate, Boc-Leu-Ser-Thr-Arg-MCA (10 mM), the amount of 7-amino-4-methyl coumarin (AMC) released by APC at 37° C. was measured fluorometrically with a fluorescence spectrophotometer (Model 650-40, Hitachi), with excitation at 380 nm and fluorescence at 440 nm being monitored. APC concentration was calculated by using as a standard the amidolytic activity of APC titrated with p-nitrophenyl-p'-guanidinobenzoate (T. Chase et al., *Biochem. Biophys. Res. Commun.*, 29, 508–514 (1967)). The initial velocity of APC production at variou's PC concentrations was determined by the best fit line for each PC concentration at the five incubation periods mentioned above. Several PC concentrations in a range from 0.5 to 6 $\mu$M were used for the kinetic study.

The values of the Michaelis constant ($K_m$) and the maximum velocity ($V_{max}$) in the Michaelis-Menten equation were obtained using three different plots, $[S]0/v$ vs. $[S]0$, $1/v$ vs. $1/[S]0$ and v vs. $v/[S]0$ (v and $[S]0$ denote the catalytic rate and the initial substrate concentration, respectively), where the best fit values were determined by the method of least squares with Taylor expansion, as described by M. Sakoda et al., *J. Biochem.*, 80, 547–555(1976).

Assay of PC Concentrations in Plasma. The PC concentration in plasma was measured according to the method of Francis et al., *Am. J. Clin. Pathol.*, 87, 619–625(1989), with minor modification. Ninety microliters of normal human plasma containing heparin (2.5 unit/ml) was incubated with 10 $\mu$l of either of the gingipains R (final concentration of enzyme and cysteine 5 nM and 1 mM, respectively) at 37° C. Ten microliters of the mixture was added to 80 μl of ACC-PCA solution (1 unit/ml distilled water), supplemented with 2.0 μM antipain, incubated for 5 min, then added to 500 μl of 50 mM Tris-HCl, pH 7.6 containing 100 mM NaCl, 2 mM $CaCl_2$, 1.2 mg/ml soybean trypsin inhibitor, 2.0 μM antipain. The amidolytic activity of APC was then measured, as described above. No amidolytic activity was produced by ACC-PCA from plasma which was preincubated with the anti-human PC-sheep IgG (100 μg/ml) at room temperature for 30 min, indicating that this antibody completely blocked PC activation.

Assay for APC Activity in Plasma. To measure plasma APC activity, 90 μl of plasma supplemented with heparin (2.5 unit/ml), or pretreated with anti-human PC-sheep IgG, was incubated with 10 μl of either of the gingipain R at 37° C. for various time periods. One hundred microliters of the mixture was then added to 500 μl of 50 mM Tris-HCl, pH 7.6, contang 100 mM NaCl, 2 mM $CaCl_2$ and 2.0 μM antipain, and the amidolytic activity was measured as described earlier. The APC activity was determined by subtracting the amidolytic activity of anti-PC-IgG-treated plasma from that of untreated plasma.

Determination of protein C Concentration. The molar concentration of purified PC was calculated using $A^{1\%}_{280nm}=14.5$ and a molecular weight of 62 kDa (W. Kisiel et al., *J. Clin. Invest.*, 64, 761–769 (1979).

Results

Figure 1B:
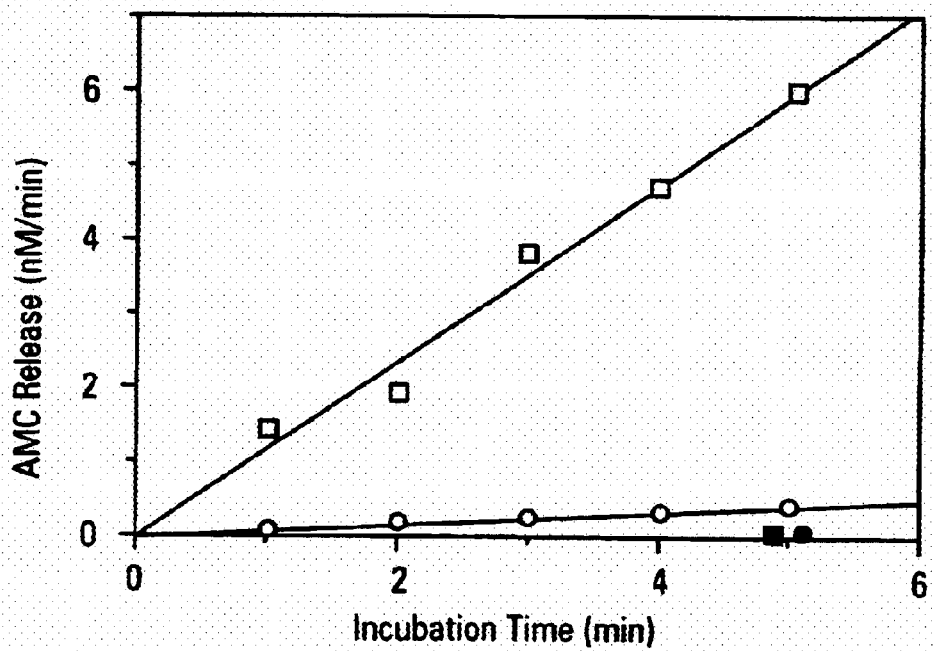

Activation of PC by gingipains R. To investigate the effect of gingipains R on PC, purified human PC was incubated with either RgpA or RgpB and APC activity measured. Both proteinases generated APC linearly in a dose- and incubation time-dependent manner (FIGS. 1A and 1B). Since TLCK-treated enzymes did not induce PC activation, it is evident that gingipains R generate APC through proteolytic cleavage of PC (FIGS. 1A and 1B). It is significant that RgpA, a complex of catalytic and adhesion/hemagglutinin domains (Pike et al., *J. Biol. Chem.*, 269, 406–411 (1994)), produced APC 14-fold more efficiently than RgpB which has only the catalytic domain (FIGS. 1A and 1B).

Figure 2A:
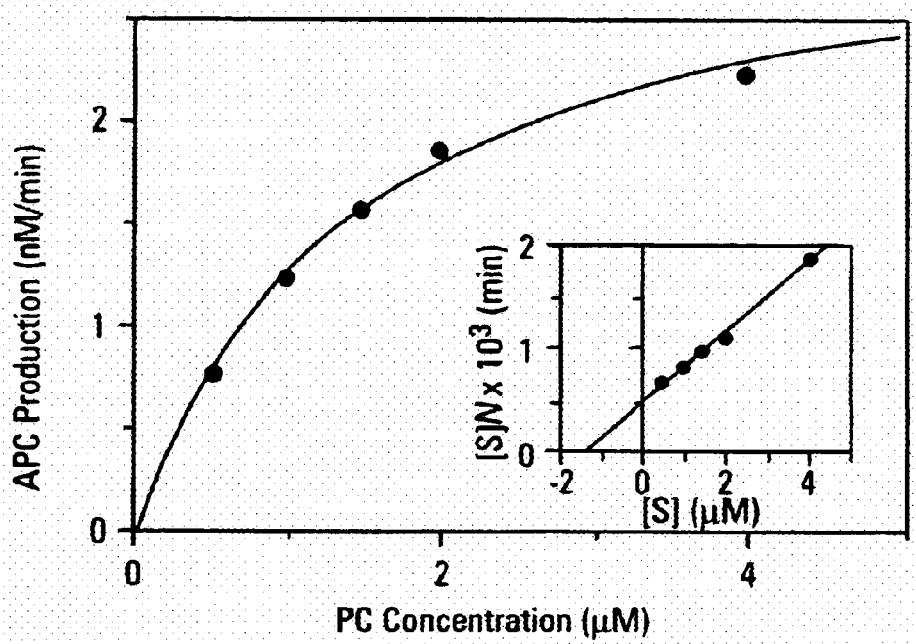
FIGS. 2A and 2B. Activation of PC by gingipains R. Ten microliters of a proteinase was added to 90 µl of PC (1 µM dissolved in 50 mM Tris-HCl, pH 7.6, 100 mM NaCl and 2 mM CaCl$_2$) and incubated at 37° C. Then, 500 µl of the above buffer supplemented with 2.0 µM leupeptin was added to stop the activation. Ten microliters of Boc-Leu-Ser-Thr-Arg-MCA (SEQ ID NO:4) (10 mM) was added to the solution and the velocity of AMC release was measured at 37° C. (A), proteinases of various concentrations were incubated with protein C for 5 minutes. The final concentrations of each proteinase are shown. (B), a proteinase (0.1 nM, the final concentration) was incubated with PC at 37° C. for various periods. (○), RgpB; (□), RgpA; (●), TLCK-inactivated RgpB; (■), TLCK-inactivated RgpA.
Figure 2B:
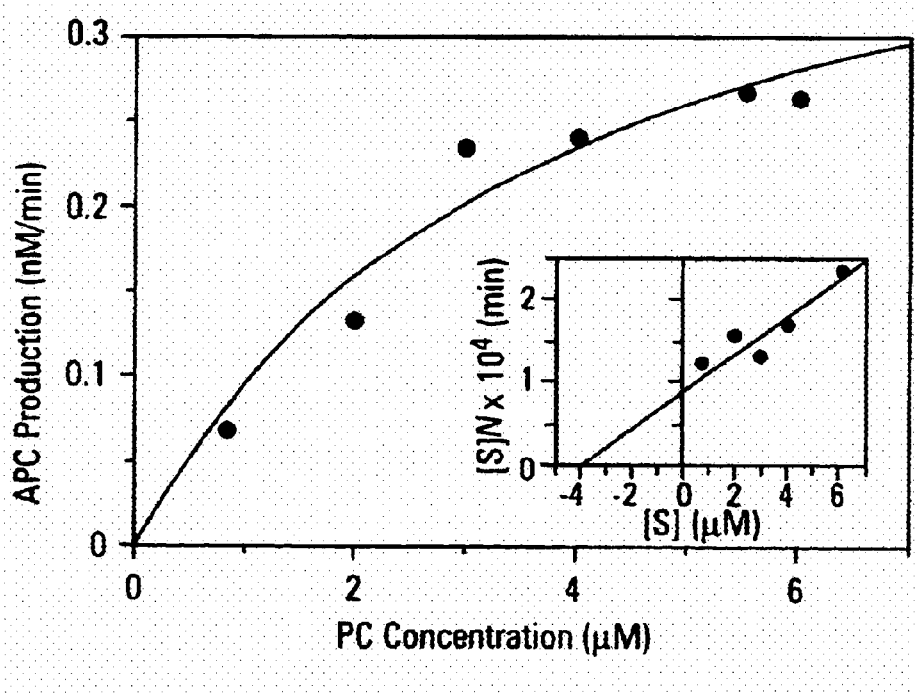

Kinetics of PC activation by gingipains R. To investigate the kinetics of PC activation by gingipains R, the values of $K_m$ and $k_{cat}$ were determined for the interaction of purified PC with either enzyme. The values of $K_m$ and $k_{cat}$ were 1.4 μM and 0.10/sec for RgpA and 3.8 μM and 0.015/sec for RgpB (FIGS. 2A and 2B). The $K_m$ values of the cysteine proteinases were lower than that of the physiological PC activator, the thrombin-thrombomodulin complex, but higher than that of the venom-derived ACC-PCA (Table 1).

TABLE I

Kinetic Constants for the Activation of human protein C

| Enzymes | $K_m$ M | $k_{cat}$ $s^{-1}$ | $k_{cat}/K_m$ $M^{-1}s^{-1}$ |
|---|---|---|---|
| RgpA | $1.4 \times 10^{-6}$ | 0.1 | $7.2 \times 10^4$ |
| 50 kDa-gingipain R | $3.8 \times 10^{-6}$ | 0.015 | $3.9 \times 10^3$ |
| thrombin-TM* | $9.8 \times 10^{-6}$ | 0.17 | $1.7 \times 10^4$ |
| ACC-PCA# | $6.0 \times 10^{-7}$ | 0.02 | $3.3 \times 10^4$ |

*Data obtained from H. H. Salem et al., J. Biol. Chem., 259, 12246–12251 (1984).
Data obtained from C. L. Orthner et al., Biochemistry, 27, 2558–2564 (1988). thrombin-TM, thrombin complexed with thrombomodulin; ACC-PCA, protein C activator from the venom of the southern copperhead snake (*Agkistrodon contortrix contortrix*).

The $k_{cat}$ value of RgpA was about 7-fold higher than that of RgpB and comparable to the values of the thrombin-thrombomodulin complex (Table I). The $k_{cat}/K_m$ value of RgpA was 18-fold higher than that of RgpB and 4- or 2-fold higher than that of the thrombin-thrombomodulin complex or ACC-PCA, respectively (Table I). These data indicate that RgpA is a more potent PC activator than RgpB and is comparable to the activities of both the thrombin-thrombomodulin and ACC-PCA complexes in PC activation.

Figure 3:
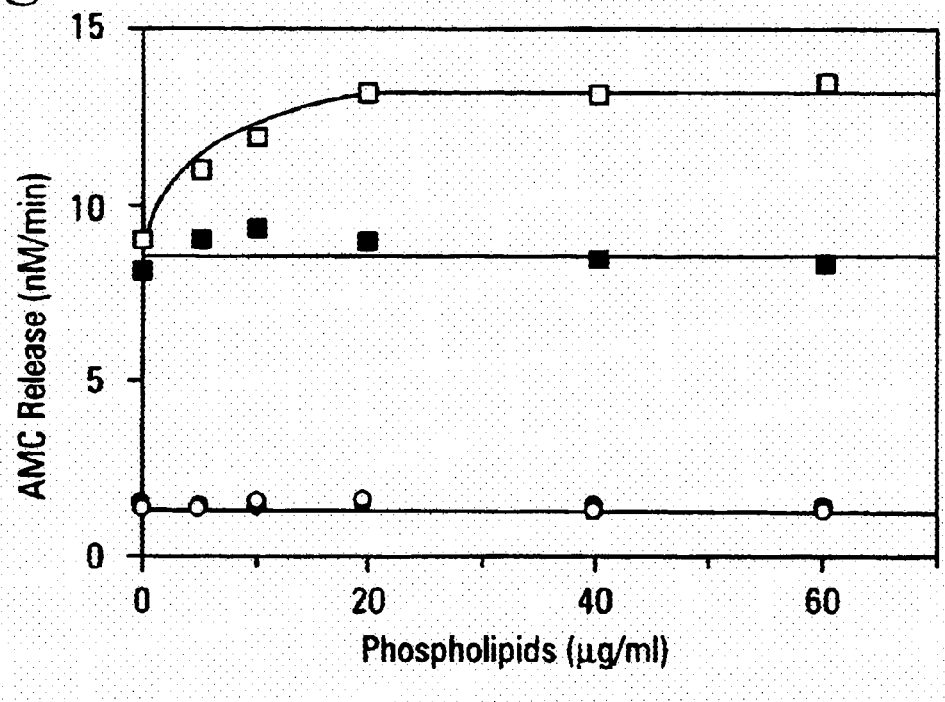
FIG. 3. Effect of phospholipids on PC activation by gingipains R. Ten microliters of a proteinase was added to a mixture of 80 µl of PC [1.25 µM dissolved in 50 mM Tris-HCl, pH 7.6, 100 mM NaCl supplemented with (open symbols) or without (solid symbols) 2 mM CaCl$_2$] and 10 µl of phospholipids. After a 5 minute incubation at 37° C., 500 µl of the above buffer supplemented with 2.0 µM leupeptin was added to the mixture to stop the activation. Ten µl of Boc-Leu-Ser-Thr-Arg-MCA (10 mM) was added to the solution and the velocity of AMC release was measured at 37° C. (○, ●), RgpB (0.2 nM, the final concentration); (□, ■), RgpA (0.1 nM, the final concentration).

Effect of phospholipids on gingipain R PC activation. Phospholipids have shown to augment PC activation by thrombin-thrombomodulin complexes (J.-M. Freyssinet et al., *Biochem. J.*, 238, 151–157 (1986)). We, therefore, investigated the effect of phospholipids on PC activation by gingipains R. APC production by RgpA increased in a phospholipid concentration-dependent manner, while no effect was seen with RgpB, and the phospholipid effect reached a plateau at concentrations above 20 μg/ml, at which level phospholipids augmented the RgpA catalyzed APC production by 1.4-fold (FIG. 3). Notably, phospholipids did not affect PC activation by RgpA when calcium ions were absent, while PC activation by either proteinase was not affected by the presence of calcium ions in the absence of phospholipids (FIG. 3). These results indicates that phospholipids can augment PC activation by RgpA but only when calcium ions are present.

Figure 5:
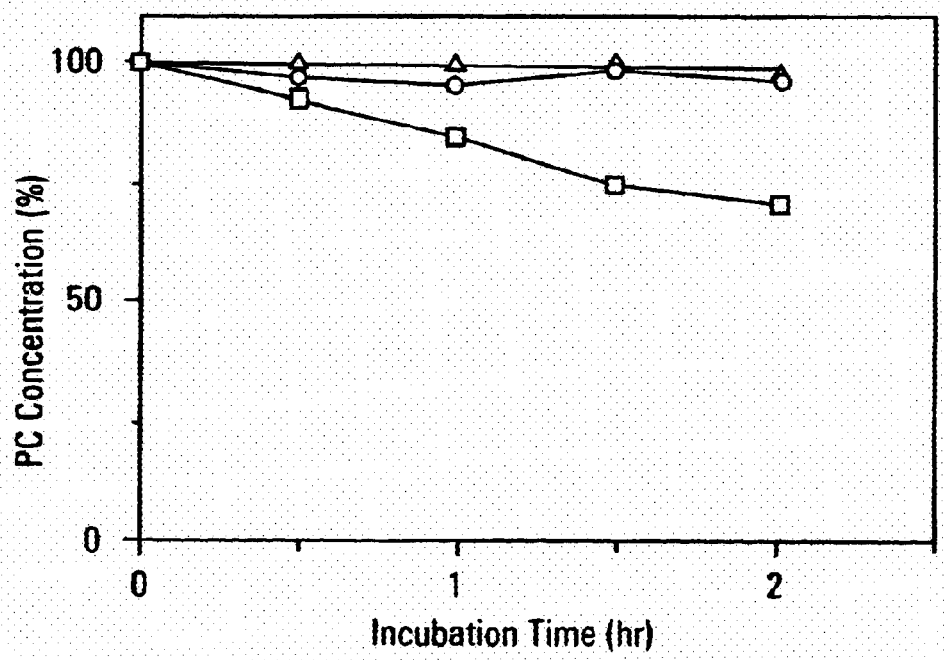
FIG. 5. Effect of gingipains R on the plasma PC level. Ten microliters of a proteinase (50 nM) was added to 90 µl of normal plasma and incubated at 37° C. for various periods. The reaction was stopped by adding 2.0 µM leupeptin. Then, 10 µl of the solution was added to 80 µl of the PCA'solution (1unit/ml) and incubated for 5 minutes at 37° C., followed by addition of 510 µl of 50 mM Tris-HCl, pH 7.6, 100 mM NaCl, supplemented with 1.4 mg/ml SBTI and 2.0 µM leupeptin. Ten microliters of Boc-Leu-Ser-Thr-Arg-MCA (10 mM) was added to the solution and the velocity of AMC release was measured at 37° C. The value was expressed by the percentage for the activity of plasma before incubation. The proteinase concentration in plasma is shown. (□), RgpA; (○), RgpB; (▼), TBS instead of a proteinase.
Figure 4A:
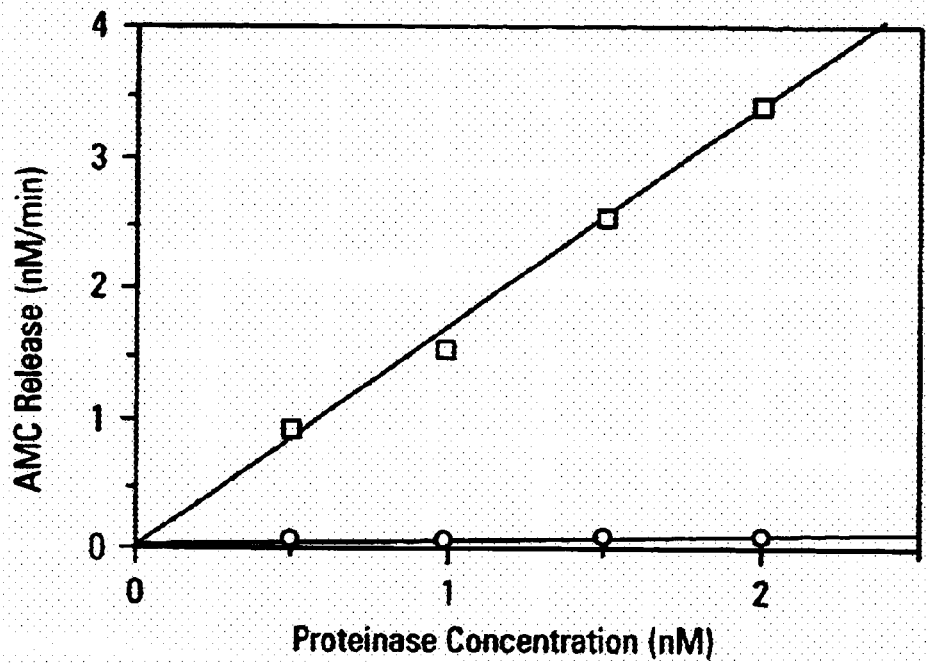
FIGS. 4A and 4B. Activation of PC in plasma by gingipains R. Ten microliters of a proteinase was added to 90 µl of plasma or PC-depleted plasma, both being supplemented with 2.5 U/ml heparin, and incubated at 37° C. Then, 30 µl of the reaction mixture was added to 570 µl of 50 mM Tris-HCl, pH 7.6, 100 mM NaCl, supplemented with 2.0 µM leupeptin. Ten microliters of Boc-Leu-Ser-Thr-Arg-MCA (10 mM) was added to the solution and the velocity of AMC release was measured at 37° C. APC activity produced by gingipain R was calculated by subtracting the amidolytic activity of PC-depleted plasma from that of non-treated plasma (A), proteinases of various concentrations were incubated with plasma for 4 minuets. The proteinase concentrations in the reaction mixture are shown. (B), a proteinase (0.5 nM, the final concentration) was incubated with plasma at 37° C. for various periods. (□), RgpA; (○), RgpB.
Figure 4B:
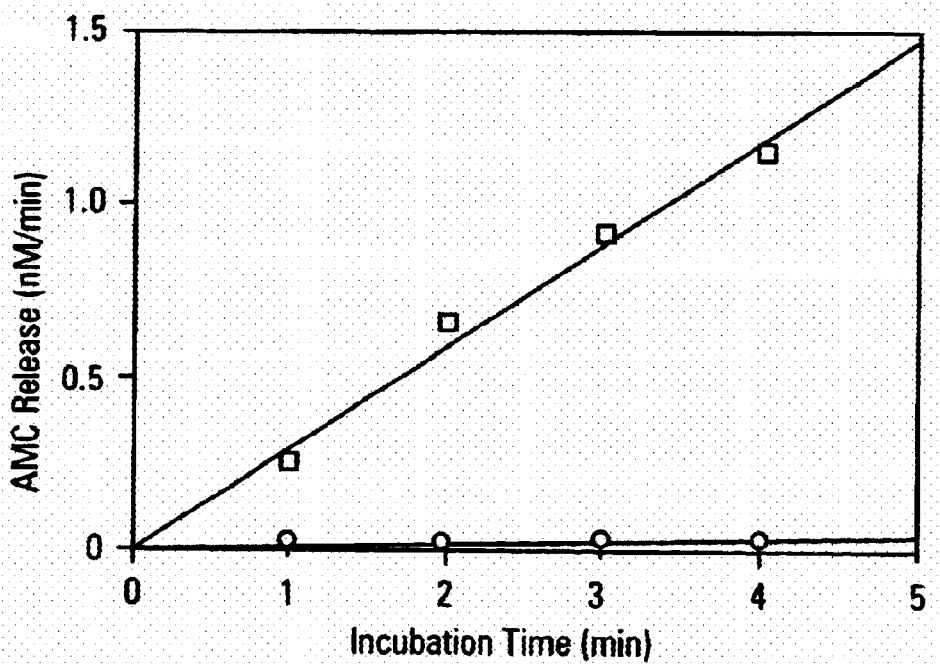

Production of APC and consequent decrease of PC in plasma by gingipains R. To study PC activation in plasma by gingipains R, human plasma was incubated with either of the two proteinases, and any APC activity generated was measured. RgpA in plasma produced APC linearly in a dose- and time-dependent manner, while with RgpB negligible APC was detected (FIGS. 4A and 4B). To determine whether PC activation by RgpA could cause consequent consumption of PC in plasma, the PC concentration was measured in plasma after incubation with each gingipain R. Consistent with the APC production activity of gingipains R in plasma (FIGS. 4A and 4B), RgpA induced a decrease in the plasma PC concentration in a time-dependent manner, while RgpB did not affect the plasma PC level even after a two-hour incubation (FIG. 5). From these data it is evident that only RgpA can cause plasma PC consumption, first through PC activation, and later by APC inactivation through complex formation with plasma inhibitors.

Discussion

One of the clinical hallmarks of periodontitis is a phenomenon described as bleeding on probing, suggesting that the coagulation cascade at the diseased site is disturbed. Our previous investigations had indicated that cysteine proteinases of *P. gingivalis*, referred to as gingipains, may contribute to this state. It was shown that gingipain K, a proteinase specific for Lys-Xaa peptide bonds could efficiently degrade fibrinogen directly in human plasma, thus markedly decreasing its clottability. In contrast, activation of factor X by gingipains R may trigger uncontrolled clot formation at periodontitis sites infected with *P. gingivalis*. In the present study we have described results which indicate that gingipains R, through activation of anticoagulant protein C, could in still another way affect hemostasis both locally and systematically.

Surprisingly, the ability of the two gingipains R to activate protein C is not equal, although RgpB retains a primary structure essentially identical to the catalytic domain of RgpA. From kinetic measurements it is apparent that the latter enzyme is 18 times more effective as a protein C activator than RgpB, predominantly because of differences in $k_{cat}$ values (Table I). These data indicate that the hemagglutinin/adhesion domain must stimulate the catalysis, and it is tempting to speculate that the binding of protein C to this domain aligns this zymogen substrate in a preferable orientation for specific proteolytic leading to active enzyme production. Such a hypothesis is further supported by the observation that RgpA can bind phospholipids (data not shown) and, together with calcium ions, stimulates PC activation by RgpA. In contrast, neither phospholipids nor Ca++ affect PC activation by RgpB, eliminating the possibility that conformational change mediated by Ca++ (D. J. Stearns et al., J. Biol. Chem., 263, 826–832 (1988)) renders PC more suitable for activation by gingipains. Because phospholipids and Ca++ are ubiquitous cellular components, they may contribute to RgpA catalyzed protein C activation in vivo. Such data support the argument that this process may take place a at periodontitis sites, because the catalytic efficiency of RgpA to activate PC ($k_{cat}/K_m$=7.2×104 M-1s-1) is four times higher than that of the physiological activator, thrombin complexed with thrombomodulin (Table I).

In the ex vivo study presented in this paper the release of APC in plasma is dependent only on the direct activation of PC by RgpA, due to the absence of the co-factors thrombomodulin and phospholipids which are necessary for PC activation by thrombin (C. T. Esmon, J. Biol. Chem., 264, 4743–4746 (1989); C. T. Esmon, Thromb. Haemost., 70, 29–35 (1993); and J.-M. Freyssinet et al., Biochem. J., 238-151–157 (1986)). In addition, heparin added to plasma would stimulate antithrombin III and heparin cofactor II mediated inhibition of factor X and thrombin. In vivo, however, either locally at the P. gingivalis infected site or, systematically, if RgpA enters the circulation any thrombin generated by this enzyme could complex with thrombomodulin on endothelial cells and activate PC.

The PC pathway is primarily a negative regulation system for coagulation. See, for example, C. T. Esmon, J. Biol. Chem., 264, 4743–4746 (1989); C. T. Esmon, Thromb. Haemost., 70, 29–35 (1993); F. J. Walker et al., Biochim. Biophys. Acta, 571, 333–342 (1979); P. B. Tracy et al., J. Biol. Chem., 258, 662–669 (1983); K. Suzuki et al., J. Biol. Chem., 258, 1914–1920 (1983); C. A. Fulcher et al., Blood, 63 486–489 (1984); D. L. Eaton et al., Biochemistry, 25, 505–512 (1986). Therefore, PC activation by RgpA would inhibit coagulation. However, down regulation of plasma clotting would be only transient, because it is apparent that activation of PC by RgpA eventually results in its consumption in plasma (FIG. 5), depleting the coagulation cascade of an important integral regulatory mechanism. In an animal model, when PC activation was blocked with a monoclonal antibody, a septic shock-like response ensued with DIC, organ damage and ultimate death being induced by challenge with E. coli at 10% the concentration which, normally would be required to elicit a lethal response (C. T. Esmon, Haematologica, 80 (suppl. 2), 49–56 (1995)). In addition, it was shown that administration of exogenous APC could protect baboons from the lethal effect of an E. coli infusion (F. B. Taylor et al., J. Clin. Invest., 79, 918–925 (1987)). Thus, it is clear that the PC system plays a crucial role in preventing the host from undergoing pathogenic coagulation, and the PC consumption, which is often observed in patients of sepsis (J. H. Griffin et al., Blood, 60, 261–264 (1982); R. B. Francis et al., Am. J. Clin. Pathol., 87, 619–625(1986); I. Kobayashi et al., Clin. Chem., 34, 2260–2263 (1988); and A. Alcaraz et al., Thromb. Res., 79, 83–93 (1995)), does lead to a thrombotic tendency, as well as predisposing to DIC. Our finding that RgpA causes plasma PC consumption (FIG. 5), together with the fact that gingipains R can induce blood coagulation through factor X activation (T. Imamura et al., J. Biol. Chem., 272, 16062–16067 (1997)), suggests the possible contribution of the bacterial proteinases to the development of DIC in sepsis.

In summary, the results presented show for the first time that, besides snake venom proteinases, bacterial proteinases are also able to activate protein C directly in plasma. In addition, from the analysis of kinetic data it is apparent that RgpA of P. gingivalis is the strongest PC activator yet described, arguing in favor of the potential for this process to occur in vivo, both locally at periodontitis sites, as well as systematically, if gingipains are able to penetrate the circulation. If PC activation by gingipains leads either locally or systematically to dysregulation of the coagulation cascade, together with activation of factor X, the two combined effects may be the biochemical link which relates the correlation now known to exist between periodontitis and cardiovascular disease.

The complete disclosures of all patents, patent applications, publications, and nucleic acid and protein database entries, including for example GenBank accession numbers and EMBL accession numbers, that are cited herein are hereby incorporated by reference as if individually incorporated. Various modifications and alterations of this invention will become apparent to those skilled in the art without departing from the scope and spirit of this invention, and it should be understood that this invention is not to be unduly limited to the illustrative embodiments set forth herein.

The complete disclosures of all patents, patent applications, publications, and nucleic acid and protein database entries, including for example GenBank accession numbers and EMBL accession numbers, that are cited herein are hereby incorporated by reference as if individually incorporated. Various modifications and alterations of this invention will become apparent to those skilled in the art without departing from the scope and spirit of this invention, and it should be understood that this invention is not to be unduly limited to the illustrative embodiments set forth herein.

Sequence Listing Free Text

SEQ ID NOs:1–3: Peptides

What is claimed is:

1. A method for producing activated protein C in a medium comprising protein C, the method comprising contacting the medium with an effective amount of an arginine-specific cysteine proteinase of bacterial origin, wherein the arginine-specific cysteine proteinase consists of the sequence of SEQ ID NO:1 or SEQ ID NO:3.

2. The method of claim 1 wherein the arginine-specific cysteine proteinase has a molecular weight of about 90–100 KDa.

3. The method of claim 1 wherein the arginine-specific cysteine-proteinase is derived from *Porphyromonas gingivalis*.

4. The method of claim 1 which is an in vivo method comprising administering to a patient an effective amount of the arginine-specific cysteine proteinase of bacterial origin.

5. The method of claim 4 wherein the patient is a human.

6. A method for producing activated protein C in a medium comprising protein C, the method comprising contacting the medium with an effective amount of an arginine-specific cysteine proteinase of bacterial origin, wherein the arginine-specific cysteine proteinase includes a catalytic domain and a hemagglutinin/adhesion domain, and the arginine-specific cysteine protcinase consists of the sequence of SEQ ID NO:1 or SEQ ID NO:3.

7. A method for producing activated protein C in blood comprising protein C, the method comprising contacting the blood with an effective amount of a polypeptide consisting of the sequence of SEQ ID NO:1 or SEQ ID NO:3.

8. A method for producing activated protein C in blood comprising protein C, the method comprising contacting the blood with an effective amount of a polypeptide encoded by a polynucleotide, the complement of which hybridizes to a polynucleotide that encodes a polypeptide consisting of the sequence of SEQ ID NO:1, SEQ ID NO:2, or SEQ ID NO:3 under standard hybridization conditions, with the proviso that the polypeptide contacting the blood does not consist of the sequence of SEQ ID NO:2 and that the polypeptide contacting the blood activates protein C in blood.

9. The method of claim 8 wherein the polynucleotide that hybridizes to the complement comprises the nucleotide sequence set forth at nuclcotides 923–3133 of Genbank Accession Number U85038.

10. The method of claim 8 wherein the polypeptide contacting the blood is an arginine-specific cysteine proteinase.

11. The method of claim 8 wherein the polypeptide contacting the blood is of bacterial origin.

12. The method of claim 11 wherein the polypeptide contacting the blood is derived from *Porphyromonas gingivalis*.

13. The method of claim 8 wherein the polypeptide contacting the blood has a molecular weight of about 90–100 kDa.

14. The method of claim 8 wherein the polypeptide contacting the blood comprises a catalytic domain and a hemagglutinin/adhesion domain.

15. A method for producing activated protein C and inhibiting blood coagulation in a patient comprising administering an effective anticoagulant amount of an arginine-specific cysteine proteinase of bacterial origin, wherein the arginine-specific cysteine proteinase consists of the sequence of SEQ ID NO:1 or SEQ ID NO:3.

16. The method of claim 15 wherein the arginine-specific cysteine proteinase has a molecular weight of about 90–100 kDa.

17. The method of claim 15 wherein the arginine-specific cysteine proteinase is derived from *Porphyromonas gingivalis*.

18. The method of claim 15 wherein the patient is a human.

19. A method for producing activated protein C and inhibiting blood coagulation in a patient comprising administering an effective anticoagulant amount of an arginine-specific cysteine proteinase of bacterial origin, wherein the arginine-specific cysteine proteinase includes a catalytic domain and a hemagglutinin/adhesion domain, and the arginine-specific cysteine proteinase consists of the sequence of SEQ ID NO:1 or SEQ ID NO:3.

20. A method for producing activated protein C and inhibiting blood coagulation in a patient comprising administering an effective anticoagulant amount of a polypeptide consisting of the sequence of SEQ ID NO:1 or SEQ ID NO:3.

21. A method for producing activated protein C and inhibiting blood coagulation in a patient comprising administering an effective anticoagulant amount of a polypeptide encoded by a polynucleotide, the complement of which hybridizes to a polynucleotide that encodes a polypeptide consisting of the sequence of SEQ ID NO:1, SEQ ID NO:2, or SEQ ID NO:3 under standard hybridization conditions, with the proviso that the administered polypeptide does not consist of the sequence of SEQ ID NO:2 and that the administered polypeptide activates protein C in blood.

22. The method of claim 21 wherein the polynucleotide that hybridizes to the complement comprises the nucleotide sequence set forth at nucleotides 923–3133 of Genbank Accession Number U85038.

23. The method of claim 21 wherein the administered polypeptide is an arginine-Specific cysteine proteinase.

24. The method of claim 21 wherein the administered polypeptide is of bacterial origin.

25. The method of claim 24 wherein the administered polypeptide is derived from *Porphyromonas gingivalis*.

26. The method of claim 21 wherein the administered polypeptide has a molecular weight of about 90–100 kDa.

27. The method of claim 21 wherein the administered polypeptide comprises a catalytic domain and a hemagglutinin/adhesion domain.

28. A method for producing activated protein C in a medium comprising protein C and cysteine, the method comprising contacting the medium with an effective amount of an arginine-specific cysteine proteinase of bacterial origin, wherein the arginine-specific cysteine proteinase consists of the sequence of SEQ ID NO:1 or SEQ ID NO:3.

29. The method of claim 28 wherein the arginine-specific cysteine proteinase has a molecular weight of about 90–100 kDa.

30. The method of claim 28 wherein the arginine-specific cysteine proteinase is derived from *Porphyromonas gingivalis*.

31. The method of claim 28 which is an in vivo method comprising administering to a patient an effective amount of the arginine-specific cysteine proteinase of bacterial origin.

32. The method of claim 31 wherein the patient is a human.

33. A method for producing activated protein C in a medium comprising protein C, the method comprising contacting the medium with an effective amount of a thrombolytic composition and an arginine-specific cysteine proteinase of bacterial origin, wherein the arginine-specific cysteine proteinase consists of the sequence of SEQ ID NO:1 or SEQ ID NO:3.

34. The method of claim 33 wherein the thrombolytic composition is selected from the group consisting of urokinase, streptokinase, tissue plasminogen activator, and combinations thereof.

35. The method of claim 33 wherein the arginine-specific cysteine proteinase has a molecular weight of about 90–100 kDa.

36. The method of claim 33 wherein the arginine-specific cysteine proteinase is derived from *Porphyromonas gingivalis*.

37. The method of claim 33 which is an in vivo method comprising administering to a patient an effective amount of the arginine-specific cysteine proteinase of bacterial origin.

38. The method of claim 37 wherein the patient is a human.

39. An in vivo method for producing activated protein C in a medium comprising protein C, the method comprising contacting the medium with an effective amount of an arginine-specific cysteine proteinase of bacterial origin, wherein the arginine-specific cysteine proteinase consists of the sequence of SEQ ID NO:1 or SEQ ID NO:3.

40. The method of claim 39 wherein the arginine-specific cysteine proteinase has a molecular weight of about 90–100 kDa.

41. The method of claim 39 wherein the arginine-specific cysteine proteinase is derived from *Porphyromonas gingivalis*.

42. A method for producing activated protein C comprising:

contacting in vitro an arginine-specific cysteine proteinase of bacterial origin with cysteine to provide an activated proteinase, and contacting an effective amount of the activated proteinase with a medium comprising protein C.

43. The method of claim 42 wherein the arginine-specific cysteine proteinase has a molecular weight of about 90–100 kDa.

44. The method of claim 42 wherein the arginine-specific cysteine proteinase is derived from *Porphyromonas gingivalis*.

45. The method of claim 42 wherein the arginine-specific cysteine proteinase consists of the sequence of SEQ ID NO:1, SEQ ID NO:2, SEQ ID NO:3, or active fragments or active modifications thereof having anticoagulant activity.

46. A method for producing activated protein C comprising:

contacting an arginine-specific cysteine proteinase of bacterial origin with cysteine in the absence of protein C to provide an activated proteinase; and contacting an effective amount of the activated proteinase with a medium comprising protein C.

47. A method for producing activated protein C comprising:

contacting in vitro an arginine-specific cysteine proteinase of bacterial origin with cysteine to provide an activated proteinase, and contacting in vivo an effective amount of the activated proteinase with a medium comprising protein C.

\* \* \* \* \*

UNITED STATES PATENT AND TRADEMARK OFFICE
CERTIFICATE OF CORRECTION

PATENT NO.    : 6,627,193 B1                                              Page 1 of 1
DATED         : September 30, 2003
INVENTOR(S)   : Travis et al.

It is certified that error appears in the above-identified patent and that said Letters Patent is hereby corrected as shown below:

<u>Column 27,</u>
Line 45, delete "KDa" and insert -- kDa --

<u>Column 28,</u>
Line 45, delete "nuclcotides" and insert -- nucleotides --

<u>Column 29,</u>
Line 34, delete "Specific" and insert -- specific --

Signed and Sealed this

Twenty-fourth Day of February, 2004

JON W. DUDAS
*Acting Director of the United States Patent and Trademark Office*

SEQUENCE LISTING

<160> NUMBER OF SEQ ID NOS: 4

<210> SEQ ID NO 1
<211> LENGTH: 1477

```
<212> TYPE: PRT
<213> ORGANISM: Porphyromonas gingivalis

<400> SEQUENCE: 1

Tyr Thr Pro Val Glu Glu Lys Gln Asn Gly Arg Met Ile Val Ile Val
1               5                   10                  15

Ala Lys Lys Tyr Glu Gly Asp Ile Lys Asp Phe Val Asp Trp Lys Asn
            20                  25                  30

Gln Arg Gly Leu Arg Thr Glu Val Lys Val Ala Glu Asp Ile Ala Ser
        35                  40                  45

Pro Val Thr Ala Asn Ala Ile Gln Gln Phe Val Lys Gln Glu Tyr Glu
    50                  55                  60

Lys Glu Gly Asn Asp Leu Thr Tyr Val Leu Leu Val Gly Asp His Lys
65                  70                  75                  80

Asp Ile Pro Ala Lys Ile Thr Pro Gly Ile Lys Ser Asp Gln Val Tyr
                85                  90                  95

Gly Gln Ile Val Gly Asn Asp His Tyr Asn Glu Val Phe Ile Gly Arg
            100                 105                 110

Phe Ser Cys Glu Ser Lys Glu Asp Leu Lys Thr Gln Ile Asp Arg Thr
        115                 120                 125

Ile His Tyr Glu Arg Asn Ile Thr Thr Glu Asp Lys Trp Leu Gly Gln
130                 135                 140

Ala Leu Cys Ile Ala Ser Ala Glu Gly Gly Pro Ser Ala Asp Asn Gly
145                 150                 155                 160

Glu Ser Asp Ile Gln His Glu Asn Val Ile Ala Asn Leu Leu Thr Gln
                165                 170                 175

Tyr Gly Tyr Thr Lys Ile Ile Lys Cys Tyr Asp Pro Gly Val Thr Pro
            180                 185                 190

Lys Asn Ile Ile Asp Ala Phe Asn Gly Gly Ile Ser Leu Val Asn Tyr
        195                 200                 205

Thr Gly His Gly Ser Glu Thr Ala Trp Gly Thr Ser His Phe Gly Thr
    210                 215                 220

Thr His Val Lys Gln Leu Thr Asn Ser Asn Gln Leu Pro Phe Ile Phe
225                 230                 235                 240

Asp Val Ala Cys Val Asn Gly Asp Phe Leu Phe Ser Met Pro Cys Phe
                245                 250                 255

Ala Glu Ala Leu Met Arg Ala Gln Lys Asp Gly Lys Pro Thr Gly Thr
            260                 265                 270

Val Ala Ile Ile Ala Ser Thr Ile Asn Gln Ser Trp Ala Ser Pro Met
        275                 280                 285

Arg Gly Gln Asp Glu Met Asn Glu Ile Leu Cys Glu Lys His Pro Asn
    290                 295                 300

Asn Ile Lys Arg Thr Phe Gly Gly Val Thr Met Asn Gly Met Phe Ala
305                 310                 315                 320

Met Val Glu Lys Tyr Lys Lys Asp Gly Glu Lys Met Leu Asp Thr Trp
                325                 330                 335

Thr Val Phe Gly Asp Pro Ser Leu Leu Val Arg Thr Leu Val Pro Thr
            340                 345                 350

Lys Met Gln Val Thr Ala Pro Ala Gln Ile Asn Leu Thr Asp Ala Ser
        355                 360                 365

Val Asn Val Ser Cys Asp Tyr Asn Gly Ala Ile Ala Thr Ile Ser Ala
    370                 375                 380

Asn Gly Lys Met Phe Gly Ser Ala Val Val Glu Asn Gly Thr Ala Thr
385                 390                 395                 400
```

-continued

```
Ile Asn Leu Thr Gly Leu Thr Asn Glu Ser Thr Leu Thr Leu Thr Val
            405                 410                 415
Val Gly Tyr Asn Lys Glu Thr Val Ile Lys Thr Ile Asn Thr Asn Gly
            420                 425                 430
Glu Pro Asn Pro Tyr Gln Pro Val Ser Asn Leu Thr Ala Thr Thr Gln
            435                 440                 445
Gly Gln Lys Val Thr Leu Lys Trp Asp Ala Pro Ser Thr Lys Thr Asn
            450                 455                 460
Ala Thr Thr Asn Thr Ala Arg Ser Val Asp Gly Ile Arg Glu Leu Val
465                 470                 475                 480
Leu Leu Ser Val Ser Asp Ala Pro Glu Leu Leu Arg Ser Gly Gln Ala
                485                 490                 495
Glu Ile Val Leu Glu Ala His Asp Val Trp Asn Asp Gly Ser Gly Tyr
                500                 505                 510
Gln Ile Leu Leu Asp Ala Asp His Asp Gln Tyr Gly Gln Val Ile Pro
                515                 520                 525
Ser Asp Thr His Thr Leu Trp Pro Asn Cys Ser Val Pro Ala Asn Leu
530                 535                 540
Phe Ala Pro Phe Glu Tyr Thr Val Pro Glu Asn Ala Asp Pro Ser Cys
545                 550                 555                 560
Ser Pro Thr Asn Met Ile Met Asp Gly Thr Ala Ser Val Asn Ile Pro
                565                 570                 575
Ala Gly Thr Tyr Asp Phe Ala Ile Ala Ala Pro Gln Ala Asn Ala Lys
                580                 585                 590
Ile Trp Ile Ala Gly Gln Gly Pro Thr Lys Glu Asp Asp Tyr Val Phe
            595                 600                 605
Glu Ala Gly Lys Lys Tyr His Phe Leu Met Lys Lys Met Gly Ser Gly
            610                 615                 620
Asp Gly Thr Glu Leu Thr Ile Ser Glu Gly Gly Ser Asp Tyr Thr
625                 630                 635                 640
Tyr Thr Val Tyr Arg Asp Gly Thr Lys Ile Lys Glu Gly Leu Thr Ala
                645                 650                 655
Thr Thr Phe Glu Glu Asp Gly Val Ala Thr Gly Asn His Glu Tyr Cys
                660                 665                 670
Val Glu Val Lys Tyr Thr Ala Gly Val Ser Pro Lys Val Cys Lys Asp
                675                 680                 685
Val Thr Val Glu Gly Ser Asn Glu Phe Ala Pro Val Gln Asn Leu Thr
                690                 695                 700
Gly Ser Ala Val Gly Gln Lys Val Thr Leu Lys Trp Asp Ala Pro Asn
705                 710                 715                 720
Gly Thr Pro Asn Pro Asn Pro Asn Pro Asn Pro Gly Thr Thr
                725                 730                 735
Thr Leu Ser Glu Ser Phe Glu Asn Gly Ile Pro Ala Ser Trp Lys Thr
                740                 745                 750
Ile Asp Ala Asp Gly Asp Gly His Gly Trp Lys Pro Gly Asn Ala Pro
                755                 760                 765
Gly Ile Ala Gly Tyr Asn Ser Asn Gly Cys Val Tyr Ser Glu Ser Phe
                770                 775                 780
Gly Leu Gly Gly Ile Gly Val Leu Thr Pro Asp Asn Tyr Leu Ile Thr
785                 790                 795                 800
Pro Ala Leu Asp Leu Pro Asn Gly Gly Lys Leu Thr Phe Trp Val Cys
                805                 810                 815
```

-continued

```
Ala Gln Asp Ala Asn Tyr Ala Ser Glu His Tyr Ala Val Tyr Ala Ser
        820                 825                 830

Ser Thr Gly Asn Asp Ala Ser Asn Phe Thr Asn Ala Leu Leu Glu Glu
        835                 840                 845

Thr Ile Thr Ala Lys Gly Val Arg Ser Pro Glu Ala Ile Arg Gly Arg
850                 855                 860

Ile Gln Gly Thr Trp Arg Gln Lys Thr Val Asp Leu Pro Ala Gly Thr
865                 870                 875                 880

Lys Tyr Val Ala Phe Arg His Phe Gln Ser Thr Asp Met Phe Tyr Ile
                885                 890                 895

Asp Leu Asp Glu Val Glu Ile Lys Ala Asn Gly Lys Arg Ala Asp Phe
            900                 905                 910

Thr Glu Thr Phe Glu Ser Ser Thr His Gly Glu Ala Pro Ala Glu Trp
        915                 920                 925

Thr Thr Ile Asp Ala Asp Gly Asp Gly Gln Gly Trp Leu Cys Leu Ser
        930                 935                 940

Ser Gly Gln Leu Asp Trp Leu Thr Ala His Gly Gly Thr Asn Val Val
945                 950                 955                 960

Ala Ser Phe Ser Trp Asn Gly Met Ala Leu Asn Pro Asp Asn Tyr Leu
                965                 970                 975

Ile Ser Lys Asp Val Thr Gly Ala Thr Lys Val Lys Tyr Tyr Tyr Ala
            980                 985                 990

Val Asn Asp Gly Phe Pro Gly Asp His Tyr Ala Val Met Ile Ser Lys
        995                 1000                1005

Thr Gly Thr Asn Ala Gly Asp Phe Thr Val Val Phe Glu Glu Thr
    1010            1015            1020

Pro Asn Gly Ile Asn Lys Gly Gly Ala Arg Phe Gly Leu Ser Thr
    1025            1030            1035

Glu Ala Asn Gly Ala Lys Pro Gln Ser Val Trp Ile Glu Arg Thr
    1040            1045            1050

Val Asp Leu Pro Ala Gly Thr Lys Tyr Val Ala Phe Arg His Tyr
    1055            1060            1065

Asn Cys Ser Asp Leu Asn Tyr Ile Leu Leu Asp Ile Gln Phe
    1070            1075            1080

Thr Met Gly Gly Ser Pro Thr Pro Thr Asp Tyr Thr Tyr Thr Val
    1085            1090            1095

Tyr Arg Asp Gly Thr Lys Ile Lys Glu Gly Leu Thr Glu Thr Thr
    1100            1105            1110

Phe Glu Glu Asp Gly Val Ala Thr Gly Asn His Glu Tyr Cys Val
    1115            1120            1125

Glu Val Lys Tyr Thr Ala Gly Val Ser Pro Lys Glu Cys Val Asn
    1130            1135            1140

Val Thr Ile Asn Pro Thr Gln Phe Asn Pro Val Lys Asn Leu Lys
    1145            1150            1155

Ala Gln Pro Asp Gly Gly Asp Val Val Leu Lys Trp Glu Ala Pro
    1160            1165            1170

Ser Ala Lys Lys Thr Glu Gly Ser Arg Glu Val Lys Arg Ile Gly
    1175            1180            1185

Asp Gly Leu Phe Val Thr Ile Glu Pro Ala Asn Asp Val Arg Ala
    1190            1195            1200

Asn Glu Ala Lys Val Val Leu Ala Ala Asp Asn Val Trp Gly Asp
    1205            1210            1215

Asn Thr Gly Tyr Gln Phe Leu Leu Asp Ala Asp His Asn Thr Phe
```

-continued

```
                1220                1225                1230

Gly Ser Val Ile Pro Ala Thr Gly Pro Leu Phe Thr Gly Thr Ala
    1235                1240                1245

Ser Ser Asn Leu Tyr Ser Ala Asn Phe Glu Tyr Leu Ile Pro Ala
    1250                1255                1260

Asn Ala Asp Pro Val Val Thr Thr Gln Asn Ile Ile Val Thr Gly
    1265                1270                1275

Gln Gly Glu Val Val Ile Pro Gly Gly Val Tyr Asp Tyr Cys Ile
    1280                1285                1290

Thr Asn Pro Glu Pro Ala Ser Gly Lys Met Trp Ile Ala Gly Asp
    1295                1300                1305

Gly Gly Asn Gln Pro Ala Arg Tyr Asp Asp Phe Thr Phe Glu Ala
    1310                1315                1320

Gly Lys Lys Tyr Thr Phe Thr Met Arg Arg Ala Gly Met Gly Asp
    1325                1330                1335

Gly Thr Asp Met Glu Val Glu Asp Asp Ser Pro Ala Ser Tyr Thr
    1340                1345                1350

Tyr Thr Val Tyr Arg Asp Gly Thr Lys Ile Lys Glu Gly Leu Thr
    1355                1360                1365

Glu Thr Thr Tyr Arg Asp Ala Gly Met Ser Ala Gln Ser His Glu
    1370                1375                1380

Tyr Cys Val Glu Val Lys Tyr Ala Ala Gly Val Ser Pro Lys Val
    1385                1390                1395

Cys Val Asp Tyr Ile Pro Asp Gly Val Ala Asp Val Thr Ala Gln
    1400                1405                1410

Lys Pro Tyr Thr Leu Thr Val Val Gly Lys Thr Ile Thr Val Thr
    1415                1420                1425

Cys Gln Gly Glu Ala Met Ile Tyr Asp Met Asn Gly Arg Arg Leu
    1430                1435                1440

Ala Ala Gly Arg Asn Thr Val Val Tyr Thr Ala Gln Gly Gly Tyr
    1445                1450                1455

Tyr Ala Val Met Val Val Val Asp Gly Lys Ser Tyr Val Glu Lys
    1460                1465                1470

Leu Ala Val Lys
    1475

<210> SEQ ID NO 2
<211> LENGTH: 492
<212> TYPE: PRT
<213> ORGANISM: Porphyromonas gingivalis

<400> SEQUENCE: 2

Tyr Thr Pro Val Glu Glu Lys Gln Asn Gly Arg Met Ile Val Ile Val
1               5                   10                  15

Ala Lys Lys Tyr Glu Gly Asp Ile Lys Asp Phe Val Asp Trp Lys Asn
                20                  25                  30

Gln Arg Gly Leu Arg Thr Glu Val Lys Val Ala Glu Asp Ile Ala Ser
            35                  40                  45

Pro Val Thr Ala Asn Ala Ile Gln Gln Phe Val Lys Gln Glu Tyr Glu
        50                  55                  60

Lys Glu Gly Asn Asp Leu Thr Tyr Val Leu Leu Val Gly Asp His Lys
65                  70                  75                  80

Asp Ile Pro Ala Lys Ile Thr Pro Gly Ile Lys Ser Asp Gln Val Tyr
                85                  90                  95
```

```
Gly Gln Ile Val Gly Asn Asp His Tyr Asn Glu Val Phe Ile Gly Arg
            100                 105                 110
Phe Ser Cys Glu Ser Lys Glu Asp Leu Lys Thr Gln Ile Asp Arg Thr
        115                 120                 125
Ile His Tyr Glu Arg Asn Ile Thr Thr Glu Asp Lys Trp Leu Gly Gln
    130                 135                 140
Ala Leu Cys Ile Ala Ser Ala Glu Gly Pro Ser Ala Asp Asn Gly
145                 150                 155                 160
Glu Ser Asp Ile Gln His Glu Asn Val Ile Ala Asn Leu Leu Thr Gln
                165                 170                 175
Tyr Gly Tyr Thr Lys Ile Ile Lys Cys Tyr Asp Pro Gly Val Thr Pro
            180                 185                 190
Lys Asn Ile Ile Asp Ala Phe Asn Gly Ile Ser Leu Val Asn Tyr
        195                 200                 205
Thr Gly His Gly Ser Glu Thr Ala Trp Gly Thr Ser His Phe Gly Thr
    210                 215                 220
Thr His Val Lys Gln Leu Thr Asn Ser Asn Gln Leu Pro Phe Ile Phe
225                 230                 235                 240
Asp Val Ala Cys Val Asn Gly Asp Phe Leu Phe Ser Met Pro Cys Phe
                245                 250                 255
Ala Glu Ala Leu Met Arg Ala Gln Lys Asp Gly Lys Pro Thr Gly Thr
            260                 265                 270
Val Ala Ile Ile Ala Ser Thr Ile Asn Gln Ser Trp Ala Ser Pro Met
        275                 280                 285
Arg Gly Gln Asp Glu Met Asn Glu Ile Leu Cys Glu Lys His Pro Asn
    290                 295                 300
Asn Ile Lys Arg Thr Phe Gly Gly Val Thr Met Asn Gly Met Phe Ala
305                 310                 315                 320
Met Val Glu Lys Tyr Lys Lys Asp Gly Glu Lys Met Leu Asp Thr Trp
                325                 330                 335
Thr Val Phe Gly Asp Pro Ser Leu Leu Val Arg Thr Leu Val Pro Thr
            340                 345                 350
Lys Met Gln Val Thr Ala Pro Ala Gln Ile Asn Leu Thr Asp Ala Ser
        355                 360                 365
Val Asn Val Ser Cys Asp Tyr Asn Gly Ala Ile Ala Thr Ile Ser Ala
    370                 375                 380
Asn Gly Lys Met Phe Gly Ser Ala Val Val Glu Asn Gly Thr Ala Thr
385                 390                 395                 400
Ile Asn Leu Thr Gly Leu Thr Asn Glu Ser Thr Leu Thr Leu Thr Val
                405                 410                 415
Val Gly Tyr Asn Lys Glu Thr Val Ile Lys Thr Ile Asn Thr Asn Gly
            420                 425                 430
Glu Pro Asn Pro Tyr Gln Pro Val Ser Asn Leu Thr Ala Thr Thr Gln
        435                 440                 445
Gly Gln Lys Val Thr Leu Lys Trp Asp Ala Pro Ser Thr Lys Thr Asn
    450                 455                 460
Ala Thr Thr Asn Thr Ala Arg Ser Val Asp Gly Ile Arg Glu Leu Val
465                 470                 475                 480
Leu Leu Ser Val Ser Asp Ala Pro Glu Leu Leu Arg
                485                 490

<210> SEQ ID NO 3
<211> LENGTH: 507
<212> TYPE: PRT
```

-continued

<213> ORGANISM: Porphyromonas gingivalis

<400> SEQUENCE: 3

```
Tyr Thr Pro Val Glu Glu Lys Glu Asn Gly Arg Met Ile Val Ile Val
1               5                   10                  15

Ala Lys Lys Tyr Glu Gly Asp Ile Lys Asp Phe Val Asp Trp Lys Asn
            20                  25                  30

Gln Arg Gly Leu Arg Thr Glu Val Lys Val Ala Glu Asp Ile Ala Ser
        35                  40                  45

Pro Val Thr Ala Asn Ala Ile Gln Gln Phe Val Lys Gln Glu Tyr Glu
    50                  55                  60

Lys Glu Gly Asn Asp Leu Thr Tyr Val Leu Leu Val Gly Asp His Lys
65                  70                  75                  80

Asp Ile Pro Ala Lys Ile Thr Pro Gly Ile Lys Ser Asp Gln Val Tyr
                85                  90                  95

Gly Gln Ile Val Gly Asn Asp His Tyr Asn Glu Val Phe Ile Gly Arg
            100                 105                 110

Phe Ser Cys Glu Ser Lys Glu Asp Leu Lys Thr Gln Ile Asp Arg Thr
        115                 120                 125

Ile His Tyr Glu Arg Asn Ile Thr Thr Glu Asp Lys Trp Leu Gly Gln
130                 135                 140

Ala Leu Cys Ile Ala Ser Ala Glu Gly Gly Pro Ser Ala Asp Asn Gly
145                 150                 155                 160

Glu Ser Asp Ile Gln His Glu Asn Val Ile Ala Asn Leu Leu Thr Gln
                165                 170                 175

Tyr Gly Tyr Thr Lys Ile Ile Lys Cys Tyr Asp Pro Gly Val Thr Pro
            180                 185                 190

Lys Asn Ile Ile Asp Ala Phe Asn Gly Gly Ile Ser Leu Val Asn Tyr
        195                 200                 205

Thr Gly His Gly Ser Glu Thr Ala Trp Gly Thr Ser His Phe Gly Thr
    210                 215                 220

Thr His Val Lys Gln Leu Thr Asn Ser Asn Gln Leu Pro Phe Ile Phe
225                 230                 235                 240

Asp Val Ala Cys Val Asn Gly Asp Phe Leu Phe Ser Met Pro Cys Phe
                245                 250                 255

Ala Glu Ala Leu Met Arg Ala Gln Lys Asp Gly Lys Pro Thr Gly Thr
            260                 265                 270

Val Ala Ile Ile Ala Ser Thr Ile Asp Gln Tyr Trp Ala Pro Pro Met
        275                 280                 285

Arg Gly Gln Asp Glu Met Asn Glu Ile Leu Cys Glu Lys His Pro Asn
    290                 295                 300

Asn Ile Lys Arg Thr Phe Gly Gly Val Thr Met Asn Gly Met Phe Ala
305                 310                 315                 320

Met Val Glu Lys Tyr Lys Lys Asp Gly Glu Asn Met Leu Asp Thr Trp
                325                 330                 335

Thr Val Phe Gly Asp Pro Ser Leu Leu Val Arg Thr Leu Val Pro Thr
            340                 345                 350

Glu Met Gln Val Thr Ala Pro Ala Asn Ile Ser Ala Ser Ala Gln Thr
        355                 360                 365

Phe Glu Val Ala Cys Asp Tyr Asn Gly Ala Ile Ala Thr Leu Ser Asp
    370                 375                 380

Asp Gly Asp Met Val Gly Thr Ala Ile Val Lys Asp Gly Lys Ala Ile
385                 390                 395                 400
```

-continued

```
Ile Lys Leu Asn Glu Ser Ile Ala Asp Glu Thr Asn Leu Thr Leu Thr
                405                 410                 415

Val Val Gly Tyr Asn Lys Val Thr Val Ile Lys Asp Val Lys Val Glu
                420                 425                 430

Gly Thr Ser Ile Ala Asp Val Ala Asn Asp Lys Pro Tyr Thr Val Ala
            435                 440                 445

Val Ser Gly Lys Thr Ile Thr Val Glu Ser Pro Ala Ala Gly Leu Thr
        450                 455                 460

Ile Phe Asp Met Asn Gly Arg Arg Val Ala Thr Ala Lys Asn Arg Met
465                 470                 475                 480

Val Phe Glu Ala Gln Asn Gly Val Tyr Ala Val Arg Ile Ala Thr Glu
                485                 490                 495

Gly Lys Thr Tyr Thr Glu Lys Val Ile Val Lys
            500                 505

<210> SEQ ID NO 4
<211> LENGTH: 4
<212> TYPE: PRT
<213> ORGANISM: Aritifical
<220> FEATURE:
<221> NAME/KEY: SITE
<222> LOCATION: (1)..(1)
<223> OTHER INFORMATION: t-Butyloxycarbonyl-Leu
<221> NAME/KEY: SITE
<222> LOCATION: (4)..(4)
<223> OTHER INFORMATION: Arg-4-Methyl-Coumaryl-7-Amide

<400> SEQUENCE: 4

Xaa Ser Thr Xaa
1
```